(12) United States Patent
Botich et al.

(10) Patent No.: US 7,524,306 B2
(45) Date of Patent: Apr. 28, 2009

(54) CATHETER INSERTION DEVICE WITH RETRACTABLE NEEDLE

(75) Inventors: Michael J. Botich, Oxnard, CA (US);
Thor R. Halseth, Simi Valley, CA (US);
John Barker, Ventura, CA (US)

(73) Assignee: MDC Investment Holdings, Inc., Wilmington, DE (US)

( * ) Notice: Subject to any disclaimer, the term of this patent is extended or adjusted under 35 U.S.C. 154(b) by 0 days.

(21) Appl. No.: 10/727,363

(22) Filed: Dec. 3, 2003

(65) Prior Publication Data

US 2004/0122373 A1  Jun. 24, 2004

Related U.S. Application Data

(63) Continuation of application No. 09/526,612, filed on Mar. 16, 2000, now abandoned, which is a continuation-in-part of application No. PCT/US99/10609, filed on May 13, 1999, and a continuation-in-part of application No. PCT/US98/24103, filed on Nov. 12, 1998, and a continuation-in-part of application No. 09/070,829, filed on Apr. 30, 1998, now Pat. No. 6,077,244.

(60) Provisional application No. 60/065,347, filed on Nov. 12, 1997, provisional application No. 60/094,801, filed on Jul. 31, 1998, provisional application No. 60/120,888, filed on Feb. 20, 1999.

(51) Int. Cl.
*A61M 5/178* (2006.01)

(52) U.S. Cl. ............... 604/164.07; 604/164.08

(58) Field of Classification Search ........... 604/162, 604/164.01, 164.07, 164.08, 164.09, 165.01, 604/171, 187, 192–198, 263, 264, 272, 533, 604/110

See application file for complete search history.

(56) References Cited

U.S. PATENT DOCUMENTS

| 4,747,831 | A | | 5/1988 | Kulli |
| 5,092,853 | A | | 3/1992 | Couvertier, II |
| 5,127,905 | A | | 7/1992 | Lemiieux |
| 5,295,974 | A | * | 3/1994 | O'Laughlin ............ 604/198 |
| 5,312,376 | A | | 5/1994 | VanHeugten |
| 5,338,305 | A | | 8/1994 | Plyley |
| 5,346,480 | A | | 9/1994 | Hess |
| 5,376,075 | A | | 12/1994 | Haughton |

(Continued)

FOREIGN PATENT DOCUMENTS

EP    0554841 A    8/1993

(Continued)

*Primary Examiner*—Kevin C. Sirmons
*Assistant Examiner*—Elizabeth R MacNeill
(74) *Attorney, Agent, or Firm*—Stoel Rives LLP

(57) ABSTRACT

A catheter insertion device is provided for inserting an over-the-needle catheter. The device includes an insertion needle that is retractable into the housing of the device after use to prevent exposure to the contaminated needle. A needle retainer releasably retains the needle in an extended position against the rearward bias of the biasing element. The needle retainer engages the hub of the catheter so that when the catheter is removed from the insertion device, the needle retainer automatically releases the needle. The biasing element then propels the needle rearwardly into the housing of the device. The device further allows the operator to intervene to delay retraction if desired.

9 Claims, 16 Drawing Sheets

U.S. PATENT DOCUMENTS

| | | | |
|---|---|---|---|
| 5,419,766 A * | 5/1995 | Chang et al. ................. 604/110 |
| 5,433,712 A | 7/1995 | Stiles |
| 5,458,658 A * | 10/1995 | Sircom ........................ 604/192 |
| 5,496,274 A | 3/1996 | Graves |
| 5,501,675 A * | 3/1996 | Erskine ....................... 604/263 |
| 5,514,100 A | 5/1996 | Mahurkar |
| 5,562,629 A | 10/1996 | Haughton |
| 5,562,634 A * | 10/1996 | Flumene et al. .............. 604/171 |
| 5,575,777 A | 11/1996 | Cover |
| 5,579,780 A | 12/1996 | Zaddini |
| 5,683,368 A | 11/1997 | Schmidt |
| 5,685,855 A | 11/1997 | Erskine |
| 5,690,619 A * | 11/1997 | Erskine ....................... 604/263 |
| 5,695,474 A | 12/1997 | Daugherty |
| 5,697,907 A | 12/1997 | Gaba |
| 5,704,914 A | 1/1998 | Stocking |
| 5,795,339 A | 8/1998 | Erskine |
| 5,989,220 A * | 11/1999 | Shaw et al. .................. 604/110 |
| 6,077,244 A * | 6/2000 | Botich et al. ................. 604/110 |
| 6,086,563 A * | 7/2000 | Moulton et al. ......... 604/164.01 |
| 6,436,070 B1 * | 8/2002 | Botich et al. ................. 604/110 |
| 6,461,362 B1 * | 10/2002 | Halseth et al. .............. 606/108 |

FOREIGN PATENT DOCUMENTS

| | | |
|---|---|---|
| EP | 0 747 087 A2 | 12/1996 |
| WO | WO 96 27403 A | 9/1996 |

\* cited by examiner

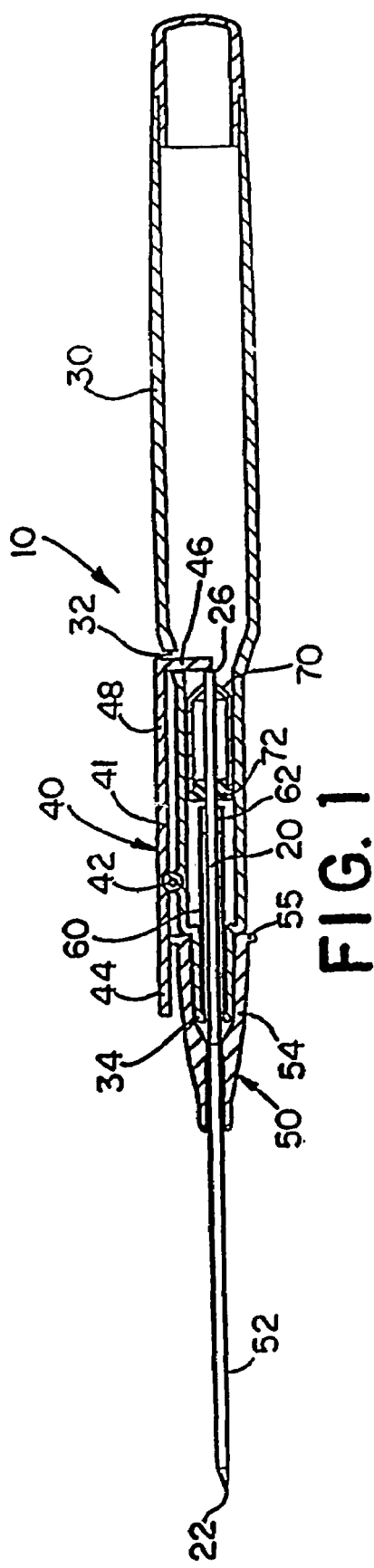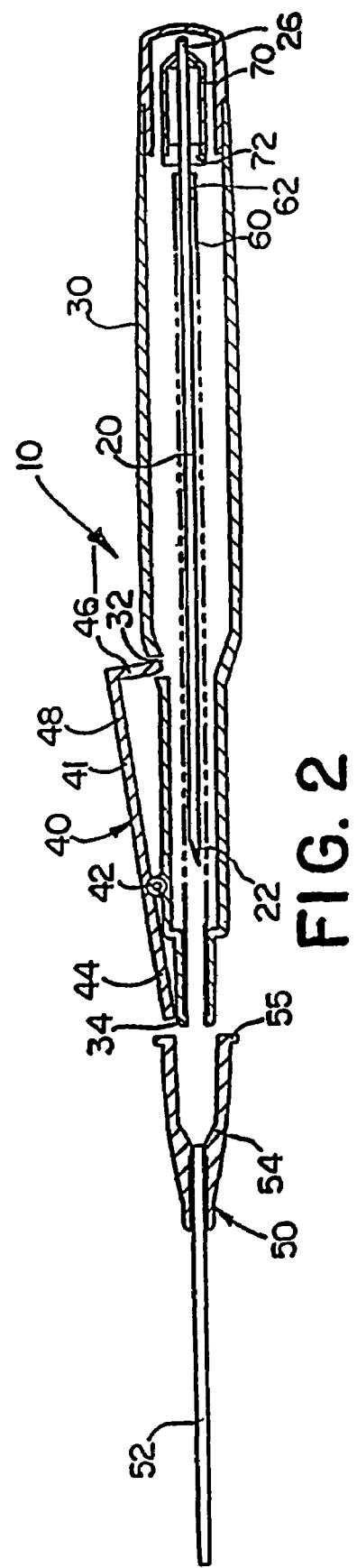

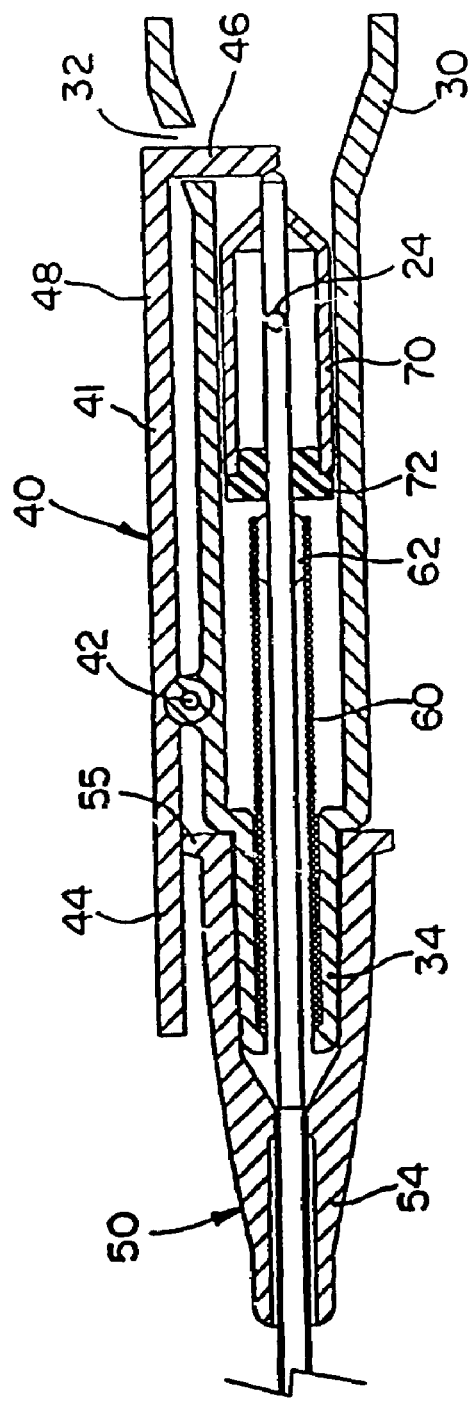
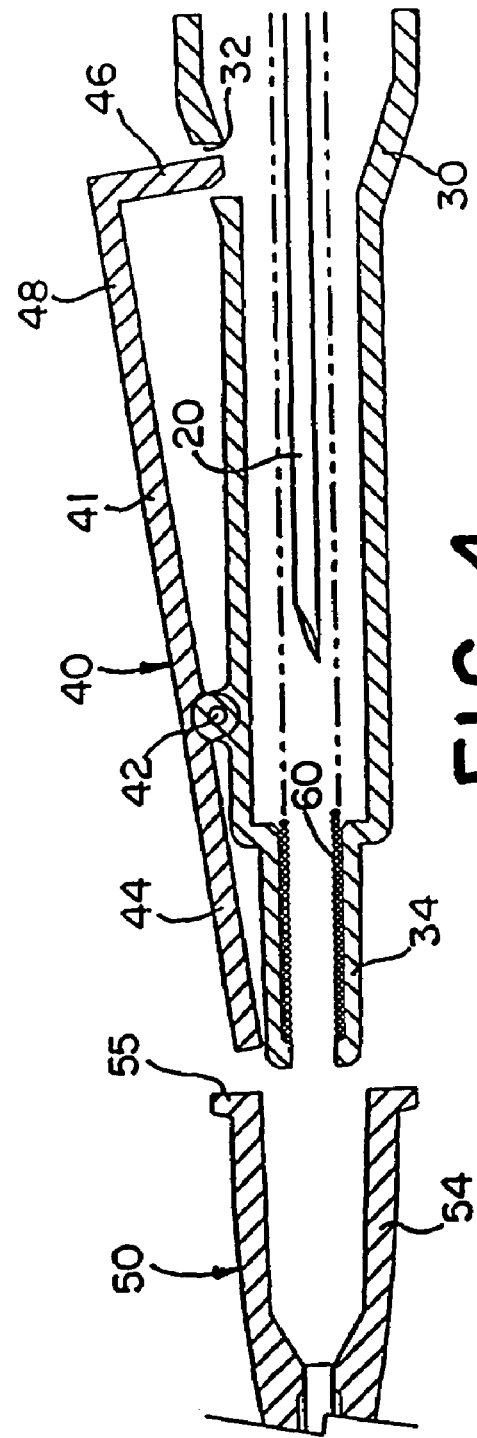

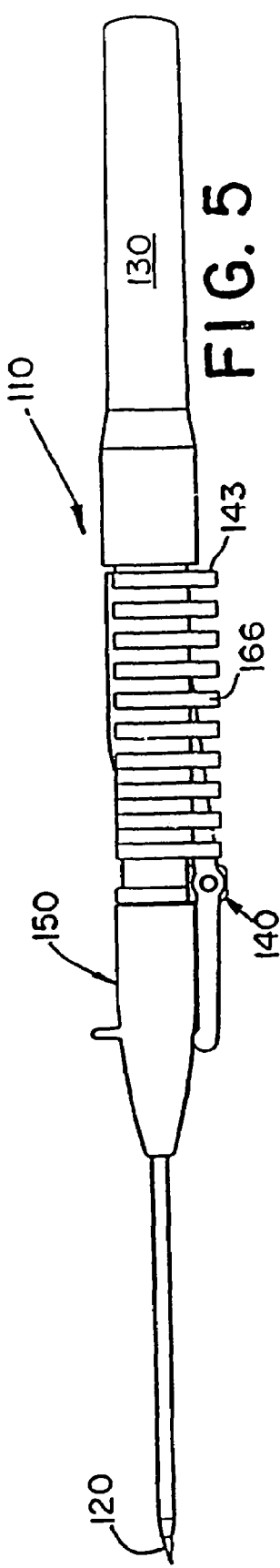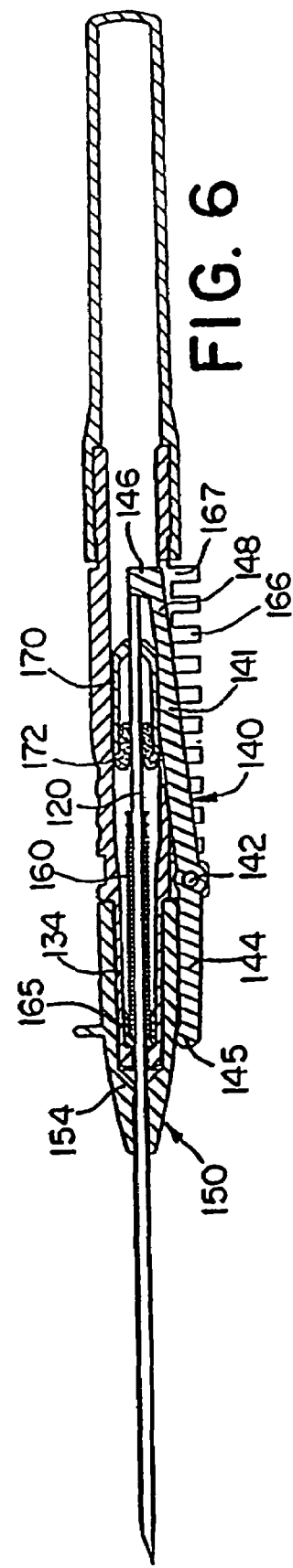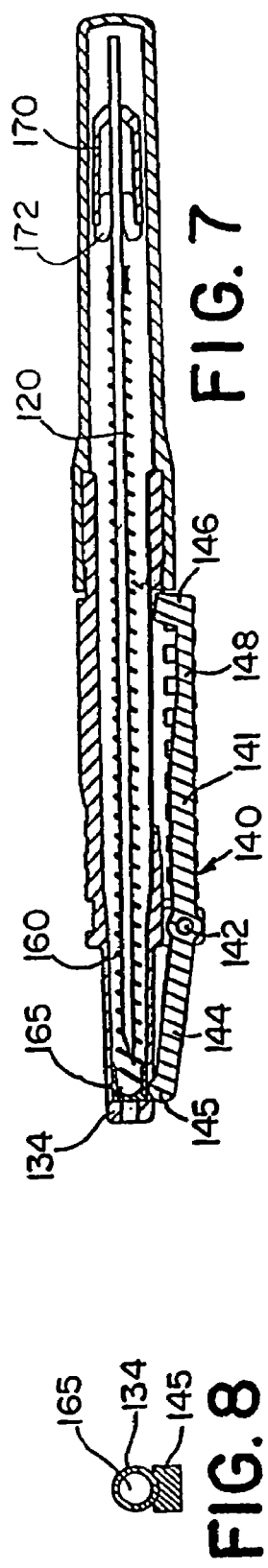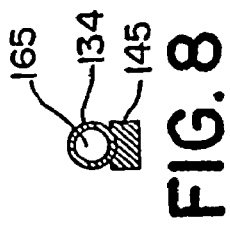

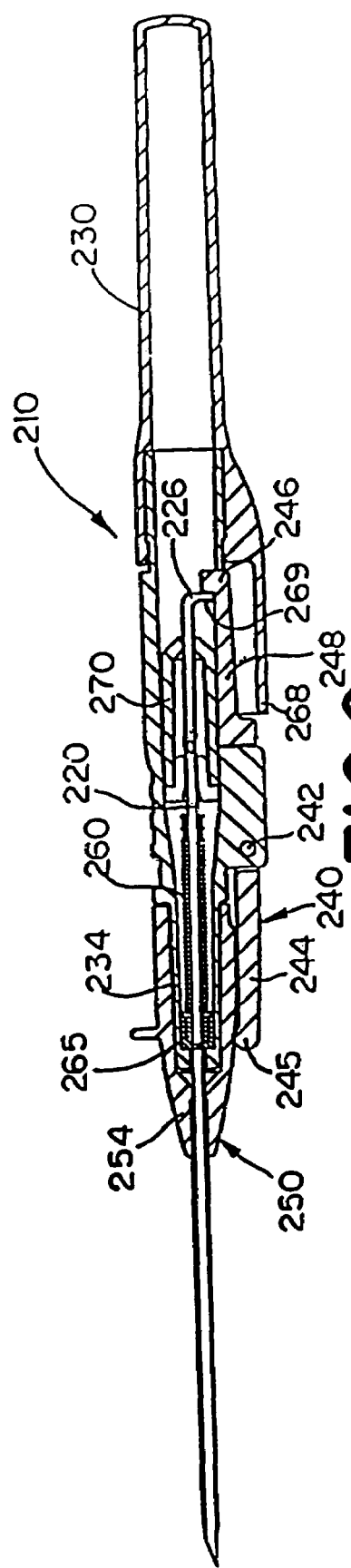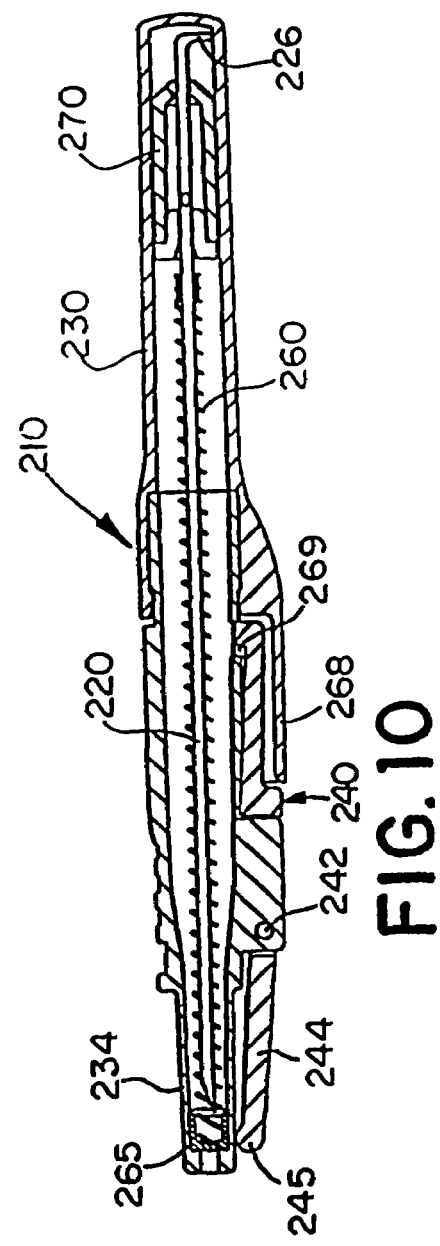

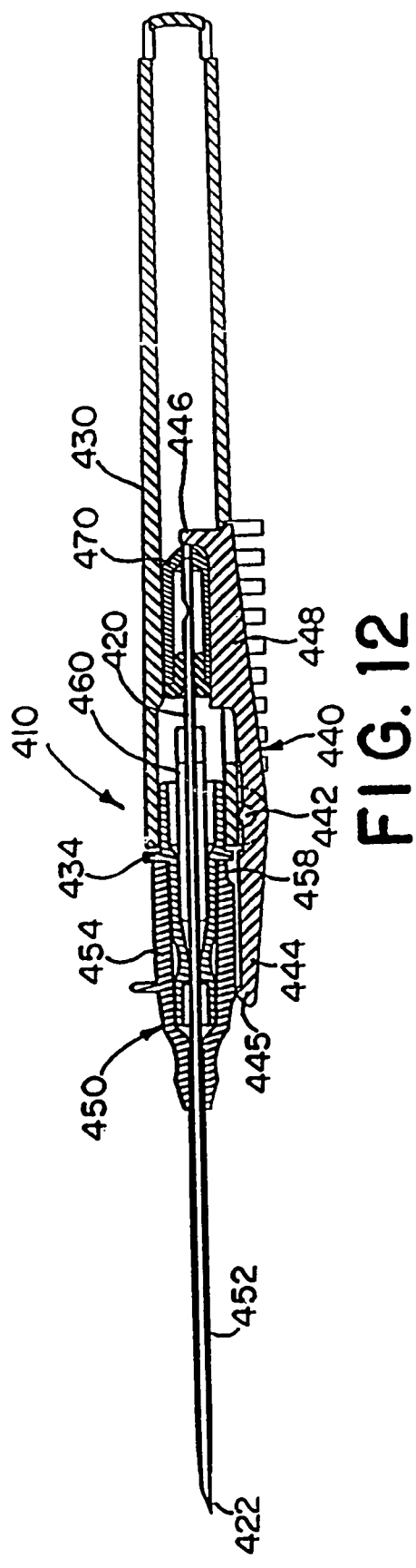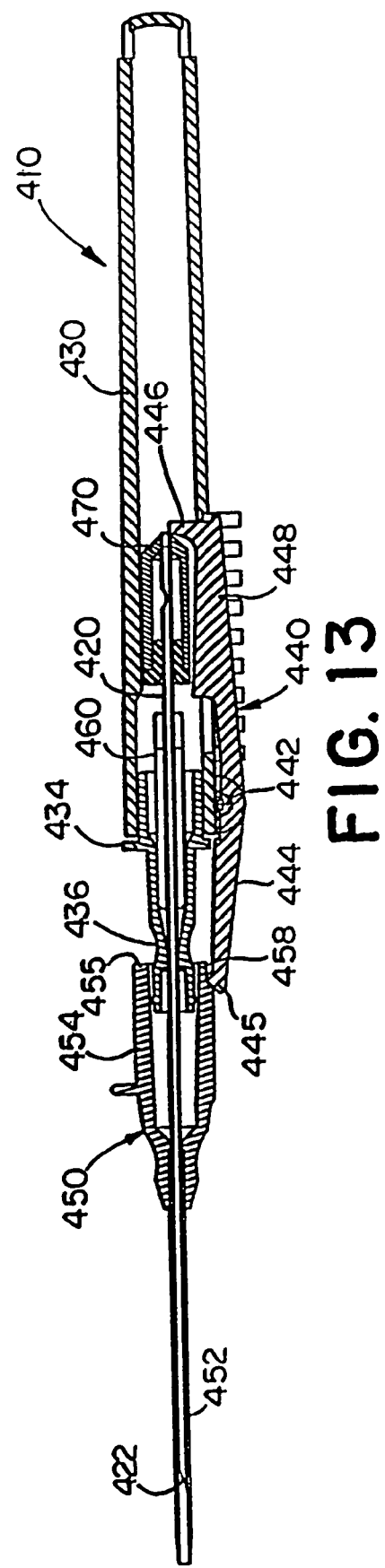

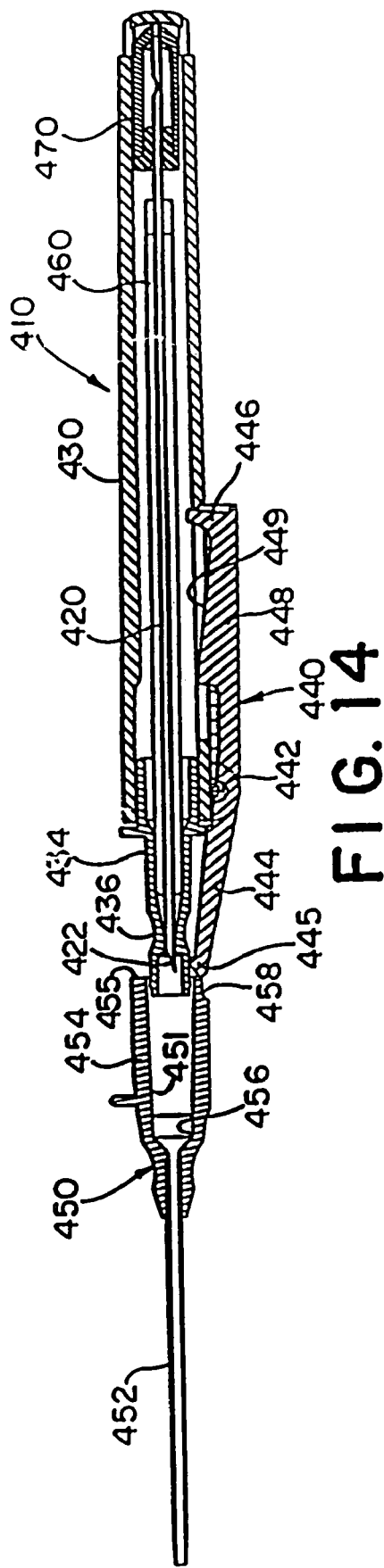

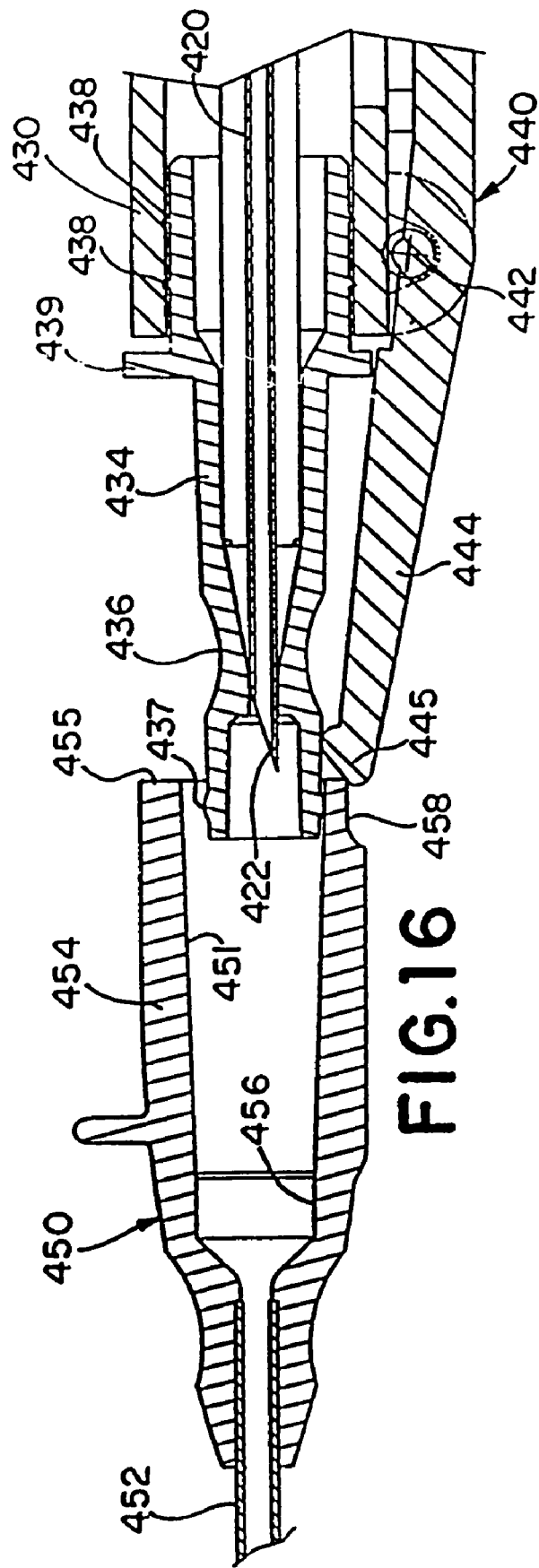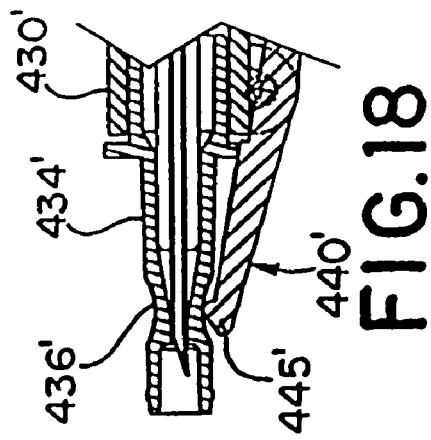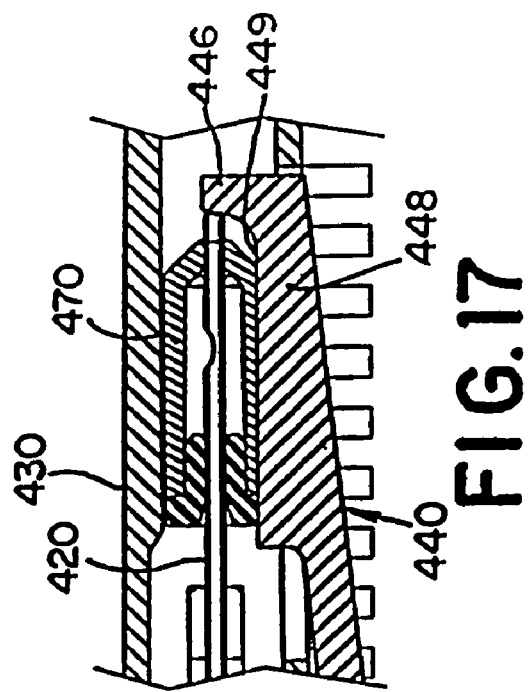

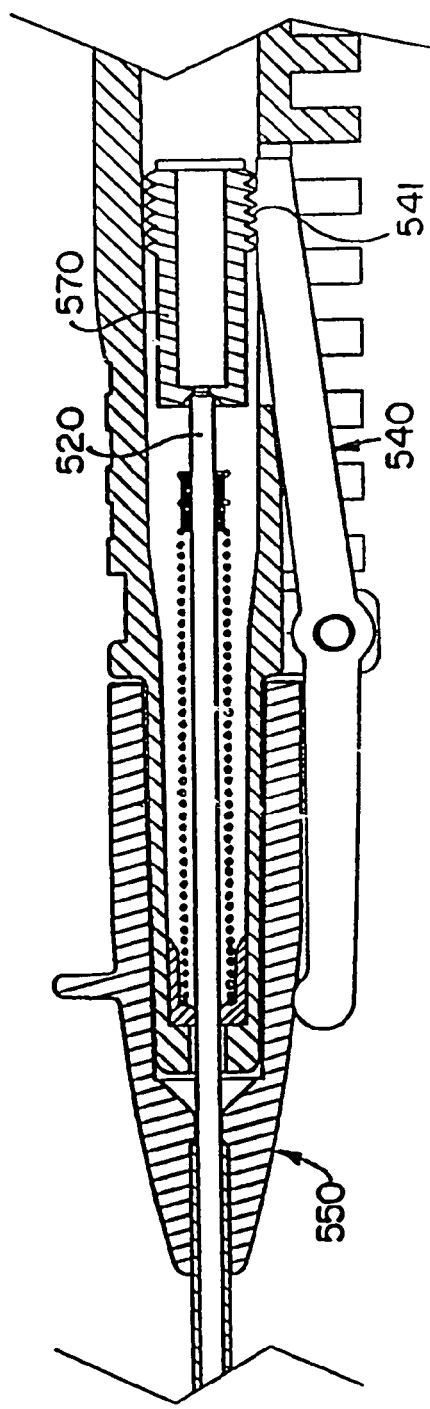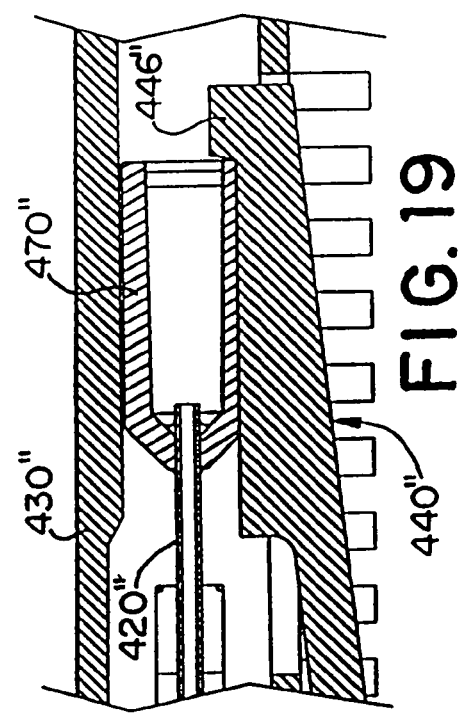

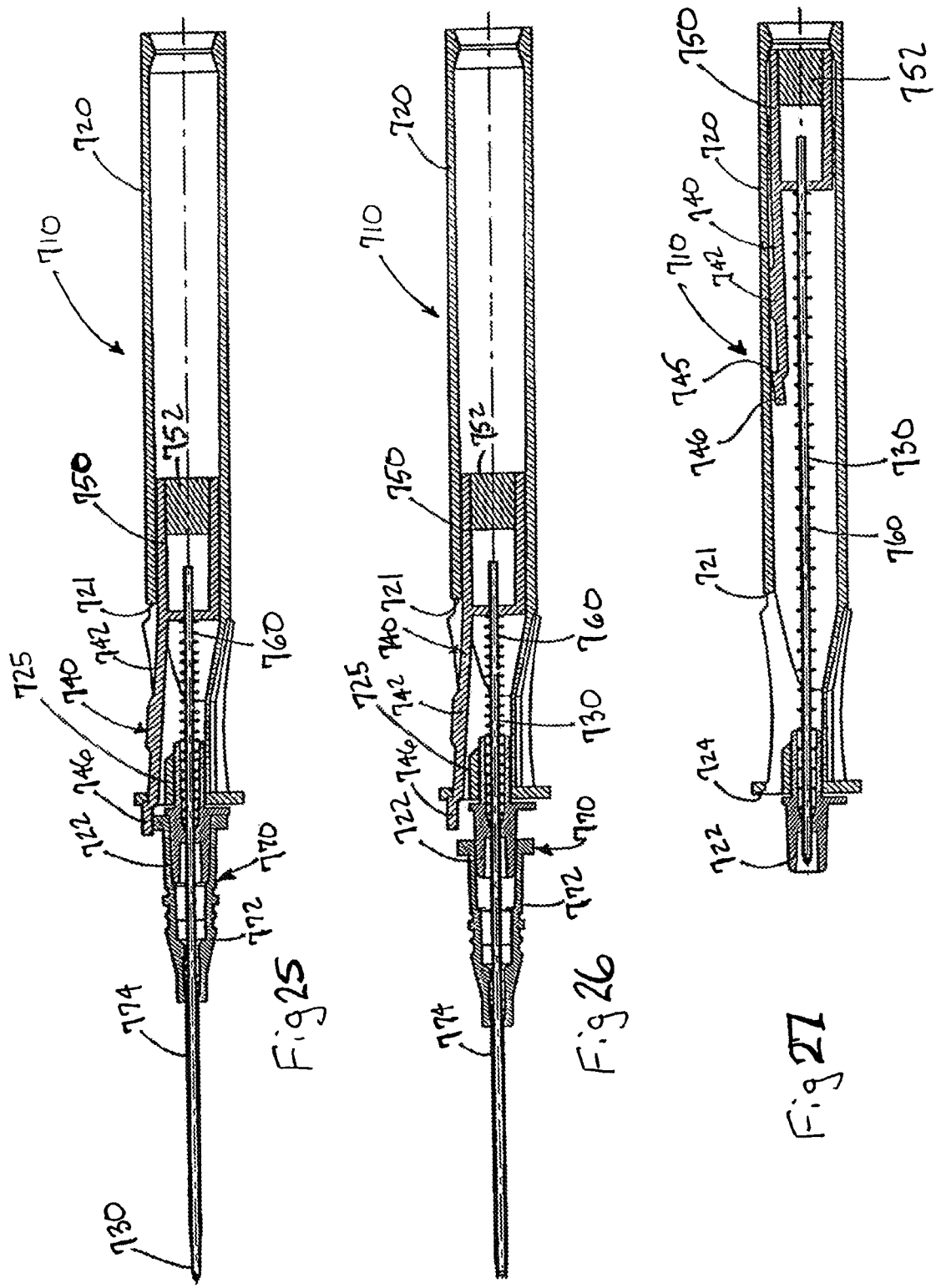

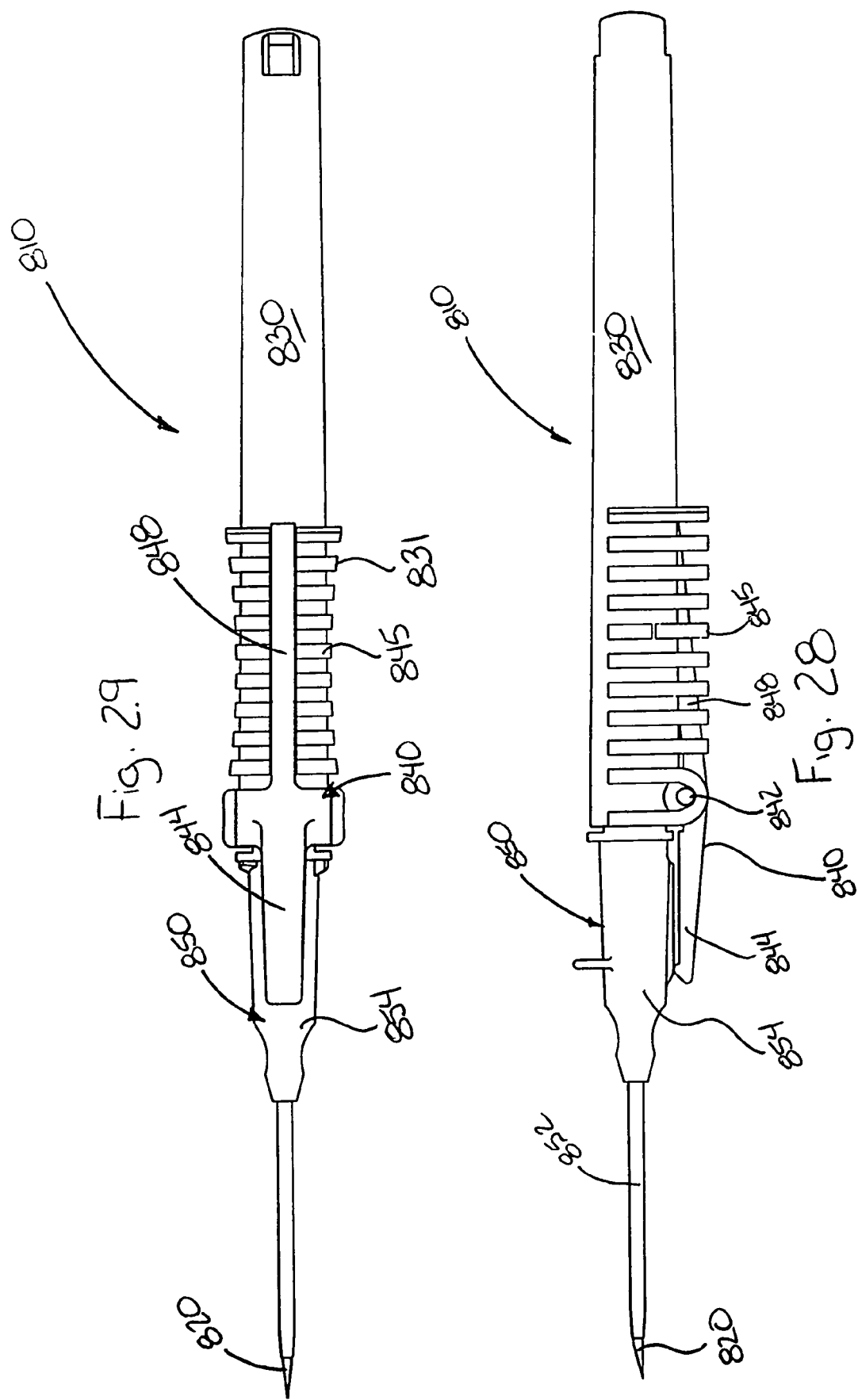

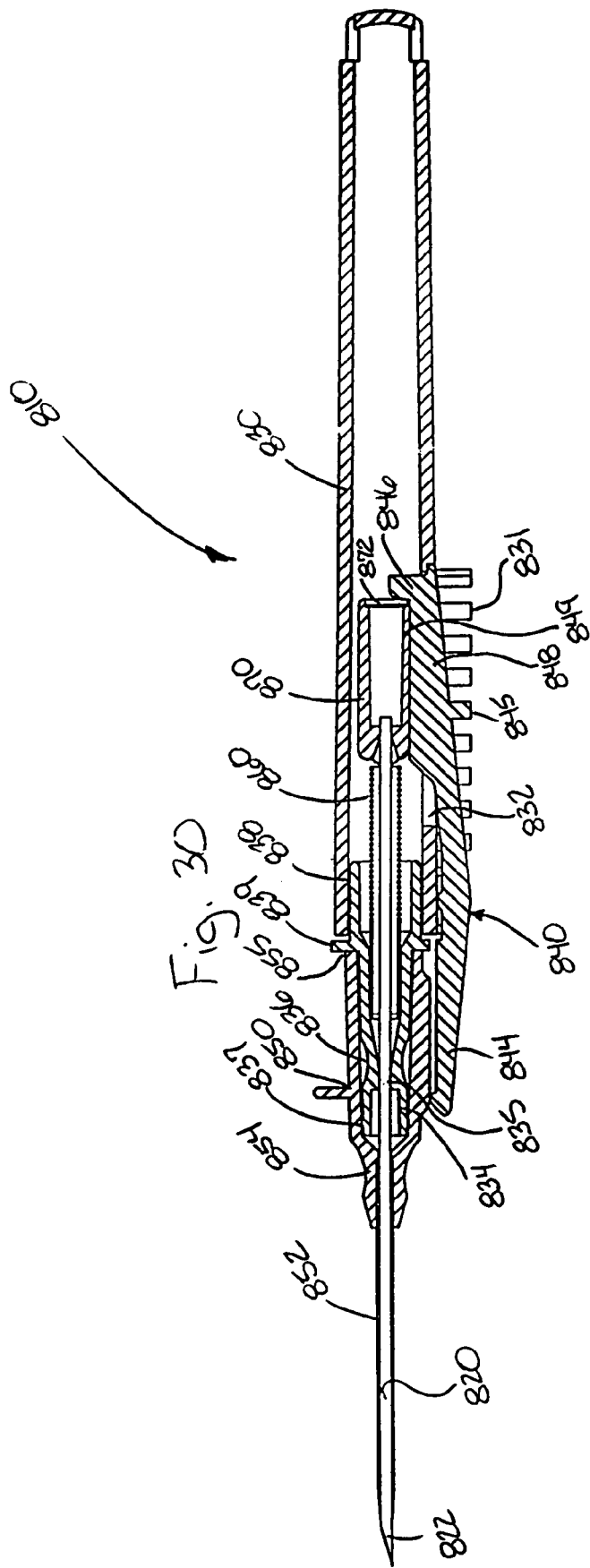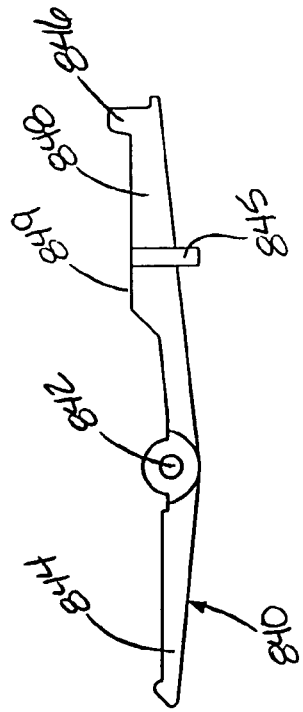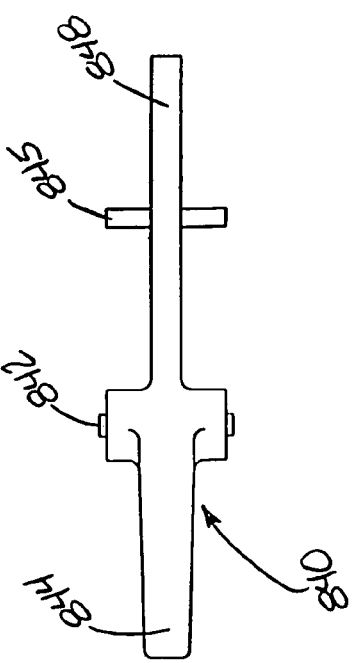

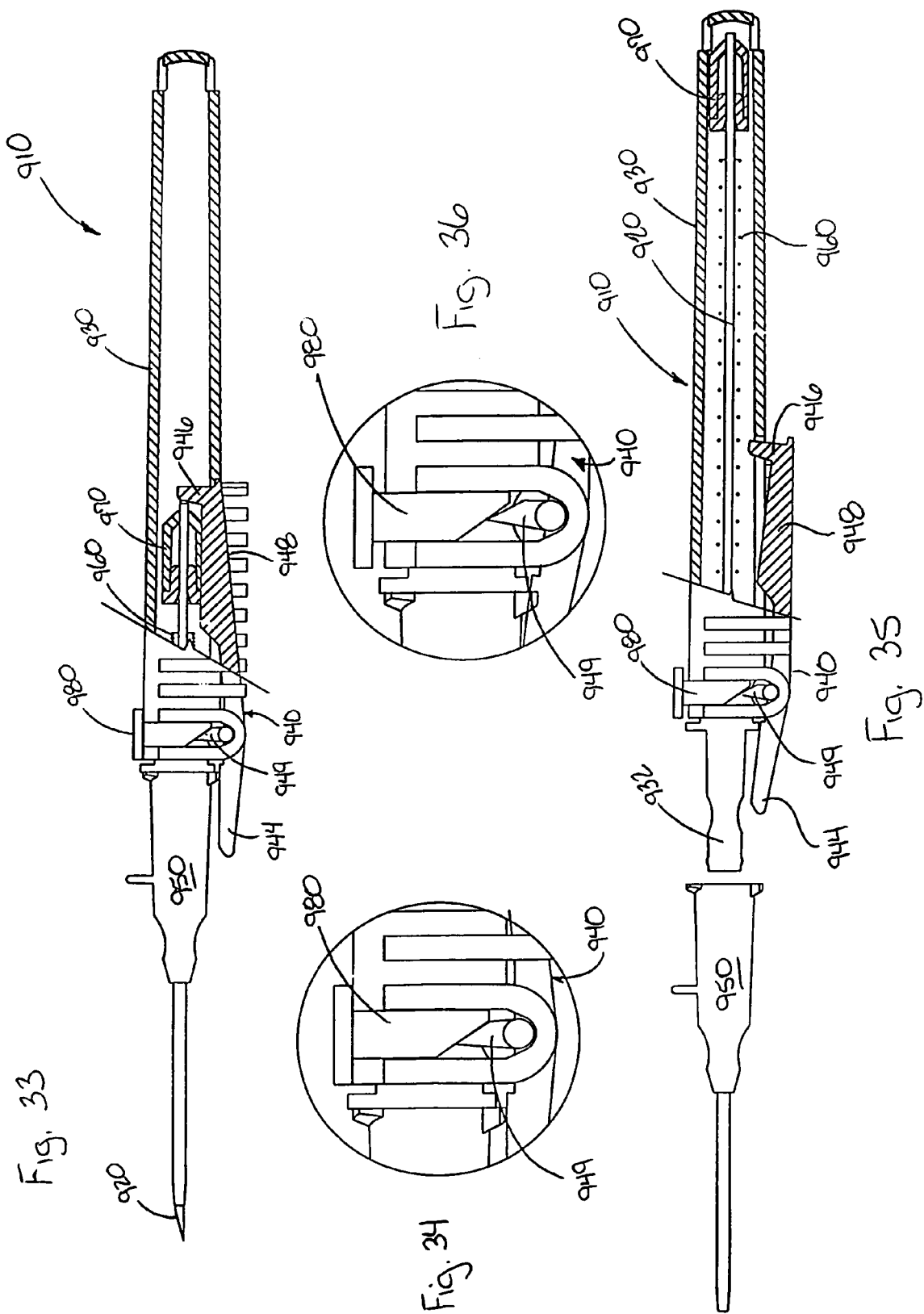

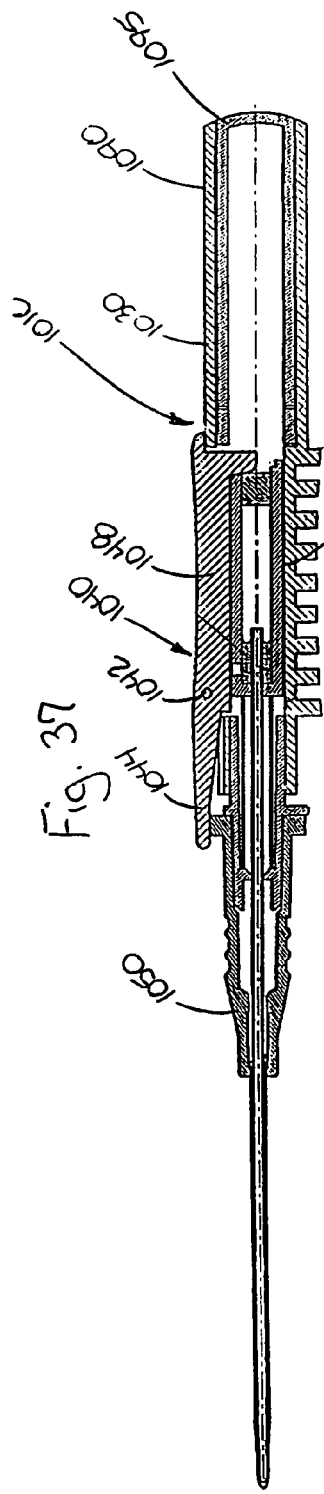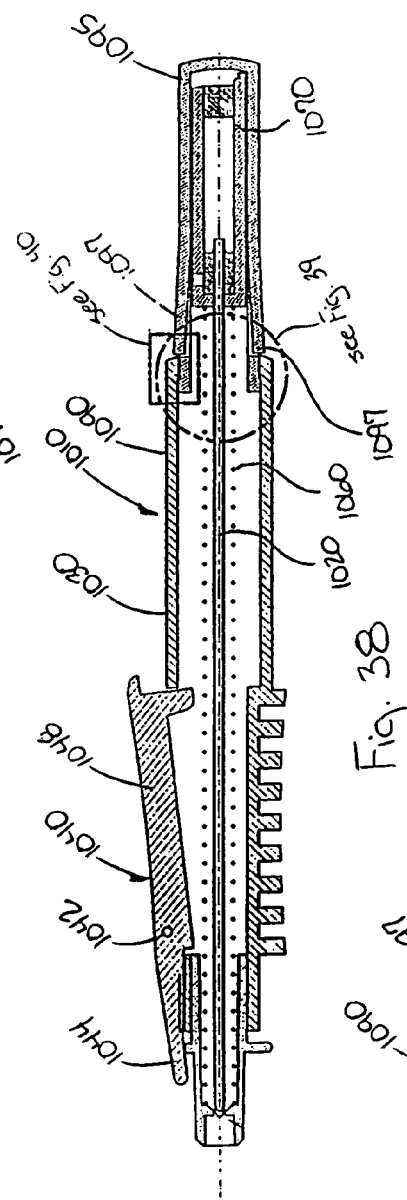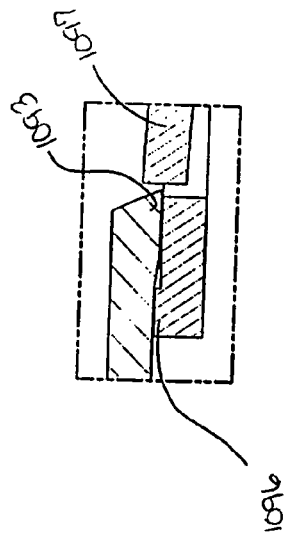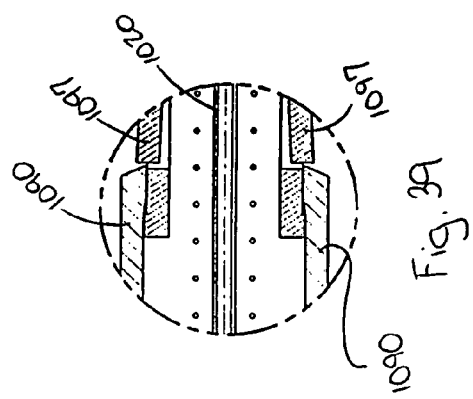

CATHETER INSERTION DEVICE WITH RETRACTABLE NEEDLE

PRIORITY STATEMENT

This application is a continuation of U.S. application Ser. No. 09/526,612, filed Mar 16, 2000, now abandoned which is a continuation-in-part of the following applications: U.S. patent application Ser. No. 09/070,829, filed Apr. 30, 1998, which issued as U.S. Pat. No. 6,077,244, which claims priority to U.S. Provisional Application No. 60/065,347, filed Nov. 12,1997; International Patent Application No. PCT/US98/24103, filed Nov. 12,1998, and International Patent Application No. PCT/US99/10609, filed May. 13, 1999, which claims priority to U.S. Provisional Application No. 60/094,801, filed Jul. 31, 1998 and U.S. Provisional Application No. 60/120,888, filed Feb. 20, 1999. Each of the foregoing applications is incorporated herein by reference.

FIELD OF THE INVENTION

The present invention relates to needle-bearing medical devices used, for example, to insert a catheter into blood vessels of patients. More specifically, the invention relates to such a device having a retractable needle feature for rendering the device non-reusable and safely disposable.

BACKGROUND OF THE INVENTION

Various types of medical devices employ a needle for piercing the skin of a patient for diagnostic or therapeutic purposes. One such device is an intravenous catheter insertion device for positioning a needle mounted catheter into a patient's blood vessel. Once the catheter is properly positioned, the catheter insertion device is withdrawn leaving the catheter in place in the blood vessel. Handling of such medical devices after the needle is withdrawn from the patient can result in transmission of various pathogens, most notably human immune virus (HIV), due to an inadvertent needle stick to medical personnel.

Since the mid-1980s, concern over the risk of accidental needle stick injuries has spawned a number of design approaches for safety needle devices. Such devices can be broadly categorized as either sliding sheath needle devices, wherein a physical barrier is positioned over the needle tip after use or as devices with-needle retraction, wherein the exposed portion of the needle is retracted into the device after use. The latter category of needle retraction devices can be further subdivided into manual and semi-automatic retraction devices. Manual retraction devices, as exemplified by U.S. Pat. No. 4,026,287 to Haller, U.S. Pat. No. 4,592,744 to Jagger, U.S. Pat. No. 4,808,169 to Haber et al. and U.S. Pat. No. 5,067,490 to Haber, require the user to pull or slide a needle-connected mechanism rearwardly to retract the needle into the device. In semi-automatic needle retraction devices, a biasing member, such as a spring, may be employed to push or pull the needle into the device in response to activation by the user of a release mechanism. Such devices are exemplified by U.S. Pat. No. 4,813,426 to Haber et al. and U.S. Pat. No. 5,125,414 to Dysarz.

U.S. Pat. No. 4,747,831 of Kulli and U.S. Pat. No. 4,900,307 of Kulli show respective catheter insertion devices and syringes with semi-automatic needle retraction. The retraction mechanism shown in the last-mentioned two patents are disclosed to be actuatable by the user upon depression of a release button after the catheter is removed from the insertion device or the needle is removed from the patient.

Of the aforementioned prior art-devices which have semi-automatic needle retraction mechanisms, all require a needle structure having an enlarged head or rim extending radially outwardly from the axis of the needle to provide a block or enlarged surface on the needle. The needle is biased toward retraction by a spring which is compressed against the block. Generally, the block, and, hence the needle, is retrained against retraction by a latching arrangement or latch mechanism. In such devices, failure of the latch mechanism or accidental activation would cause inability to retract the needle or premature retraction of the needle occurs. Hence, it would be desirable to provide an automatic needle retraction mechanism in which the latch mechanism operates in a simple fail safe manner.

In addition, the prior art semi-automatic devices require manual actuation by the operator. In many situations, such as an emergency situation, the operator is distracted or rushed so that the manual step necessary to effectuate retraction is not performed, either intentionally or unintentionally. In such instances, the used needle remains exposed, creating a risk of an inadvertent needle stick. Therefore, it would be desirable to provide an automatic needle retraction mechanism in which needle retraction is effectuated by normal operation of inserting the catheter into the patient, without the need to perform a separate manual step. It is further desirable to provide a device with a limited number of components so that the device can be produced cost effectively.

SUMMARY OF THE INVENTION

With foregoing in mind, the present invention provides a medical device having a hollow housing and a catheter mounted on the housing. The device includes a needle operable between an extended position extending forwardly from the housing and a retracted position in which the needle is enclosed in the housing. A biasing element biases the needle toward the retracted position. A lever pivots between a locked position and an unlocked position. The lever has a forward portion and a rearward portion. The forward portion engages the catheter thereby preventing the lever from pivoting into the unlocked position. The rearward portion retains the needle against the bias of the biasing element. Upon removal of the catheter from the housing, the catheter disengages the lever thereby allowing the lever to pivot into the unlocked position. The biasing element then propels the needle rearwardly into the housing. The device may further include an exposed surface that the operator can engage to delay retraction if desired.

The present invention also provides a method for inserting an intravenous catheter. The method includes the steps of providing a catheter insertion device having a housing, a catheter hub removably mounted on the housing, a needle, and a needle retainer for releasably retaining the needle so that the needle projects forwardly from the housing. The catheter is disengaged from its engagement with the housing. The needle retainer is selectively manually engaged to impede retraction of the needle, and the selective manual engagement with the needle retainer is released to disengage the needle retainer and the needle. After the needle is released, the needle is retracted into the housing.

BRIEF DESCRIPTION OF THE DRAWINGS

The foregoing summary as well as the following detailed description of the preferred embodiments of the present invention will be better understood when read in conjunction with the appended drawings, in which:

FIG. 1 is a side sectional view of a catheter insertion device with an insertion needle projecting forwardly into a catheter prior to use;

FIG. 2 is a side sectional view of the catheter insertion device illustrated in FIG. 1, showing the catheter removed and the needle retracted into the device;

FIG. 3 is an enlarged fragmentary sectional view of the device illustrated in FIG. 1;

FIG. 4 is an enlarged fragmentary sectional view of the device illustrated in FIG. 2;

FIG. 5 is a side elevational view of an alternate embodiment of a catheter insertion device with an insertion needle projecting forwardly into a catheter prior to use;

FIG. 6 is a side sectional view of the device illustrated in FIG. 5;

FIG. 7 is a side sectional view of the device illustrated in FIG. 6, with the catheter removed and showing the needle retracted into the device;

FIG. 8 is a sectional view of the device illustrated in FIG. 7, taken along the line 8-8;

FIG. 9 is a side sectional view of a second alternate embodiment of a catheter insertion device with an insertion needle projecting forwardly into a catheter prior to use;

FIG. 10 is a side sectional view of the device illustrated in FIG. 9, with the catheter removed and showing the needle retracted into the device;

FIG. 12 is a side sectional view of a fourth alternate embodiment of a catheter insertion device with an insertion needle projecting forwardly into a catheter prior to use;

FIG. 13 is a side sectional view of the catheter insertion device illustrated in FIG. 12, showing the catheter partially removed;

FIG. 14 is a side sectional view of the device illustrated in FIG. 12, with the catheter removed, and showing the insertion needle retracted into the device;

FIG. 15 is a side sectional view of the device illustrated in FIG. 14 with the catheter reattached to the device after the needle has been retracted;

FIG. 16 is an enlarged fragmentary sectional view of the tip of the device illustrated in FIG. 12;

FIG. 17 is an enlarged fragmentary sectional view of the device illustrated in FIG. 12, showing details of the needle retainers;

FIG. 18 is an enlarged fragmentary view of the device illustrated in FIG. 12 having a modified needle retainer;

FIG. 19 is an enlarged fragmentary sectional view of the device illustrated in FIG. 12 having an alternate connection between the needle retainer and the insertion needle;

FIG. 20 is a side sectional view of another alternate embodiment of a catheter insertion device with the insertion needle projecting forwardly into a catheter prior to use;

FIG. 25 is a cross-sectional view of a sixth alternate embodiment of a catheter insertion device having a retractable needle;

FIG. 26 is a cross-sectional view of the device shown in FIG. 25, illustrating the device with the catheter removed prior to retraction of the needle;

FIG. 27 is a cross-sectional view of the device shown in FIG. 25, illustrating the device after retraction of the needle;

FIG. 28 is a side elevational view of a seventh alternate embodiment of a catheter insertion device with a retractable needle according to the present invention;

FIG. 29 is a bottom plan view of the catheter insertion device illustrated in FIG. 28;

FIG. 30 is a sectional view of the catheter insertion device illustrated in FIG. 28;

FIG. 31 is a bottom plan view of a needle retainer of the catheter insertion device illustrated in FIG. 28;

FIG. 32 is a side elevational view of the catheter insertion device illustrated in FIG. 31;

FIG. 33 is a side elevational view partially in section of a eighth alternate embodiment of a catheter insertion device with a retractable needle according to the present invention;

FIG. 34 is an enlarged fragmentary view of the catheter insertion device illustrated in FIG. 33, illustrating a locking button in a locked position;

FIG. 35 is a side elevational view partially in section of the catheter insertion device illustrated in FIG. 33, showing the needle in a retracted position;

FIG. 36 is an enlarged fragmentary view of the catheter insertion device illustrated in FIG. 35, illustrating the locking button in an unlocked position;

FIG. 37 is a sectional view of a ninth alternate embodiment of a catheter insertion device with a retractable needle according to the present invention;

FIG. 38 is a sectional view of the catheter insertion device illustrated in FIG. 37, illustrating the needle in a retracted position;

FIG. 39 is an enlarged fragmentary sectional view of the catheter insertion device illustrated in FIG. 38; and FIG. 40 is an enlarged fragmentary sectional view of the catheter insertion device illustrated in FIG. 38.

DETAILED DESCRIPTION OF THE INVENTION

Figure 11:
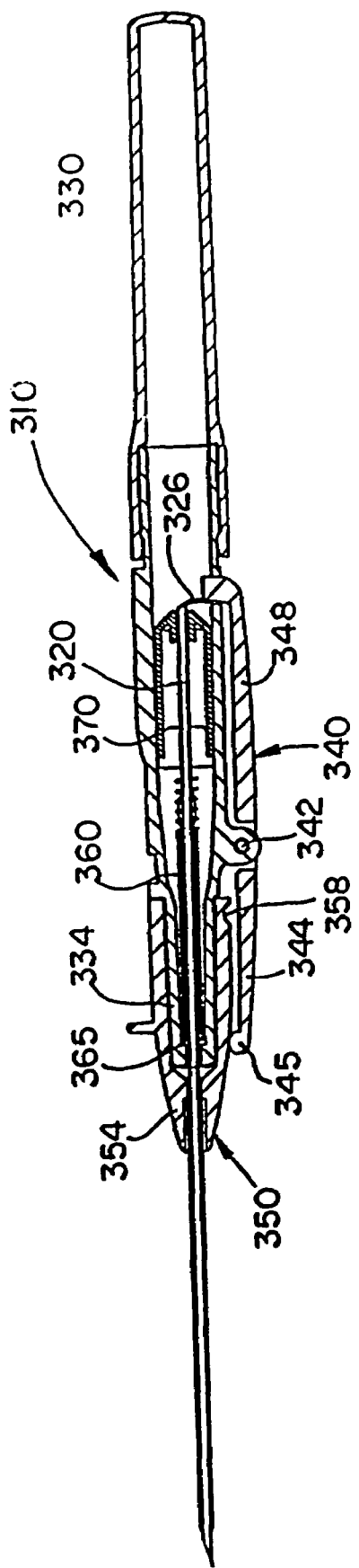
FIG. 11 is a side sectional view of a third alternate embodiment of a catheter insertion device with an insertion needle projecting forwardly into a catheter prior to use.

Referring now to FIGS. 1-4 in general and to FIG. 1 specifically, there is shown a catheter insertion device 10 for inserting a catheter 50 into a patient. The device 10 has a needle 20 to guide the catheter 50 into a vessel of the patient. The insertion device 10 is adapted to automatically retract the needle 20 inside the insertion device 10 when the operator removes the catheter 50 from the device. This automatic retraction feature renders the needle non-reusable and safely disposable.

The catheter insertion device 10 includes a generally cylindrical hollow barrel or housing 30 having a reduced diameter forward tip portion 34. The needle 20 is releasably retained so that the forward end of the needle projects forwardly through a hole in the barrel tip 34. The needle is operable between an extended position and a retracted position. In the retracted position, the needle is enclosed within the housing.

The catheter 50 is initially mounted on the forward end of the catheter insertion device 10 with the needle 20 projecting from the front of the device through the catheter. The catheter 50 comprises a cannula 52 and a hub 54. The cannula 52 sheaths or receives the front portion of needle 20, so that the sharpened point of the needle extends slightly beyond the open end of the cannula.

Referring to FIG. 3, a cylindrical chamber 70 is attached to the needle. The chamber 70 forms a flashback chamber. The flashback chamber 70 is attached near the rear end 26 of the needle 20 so that the flashback chamber encloses a port 24 formed through the side of the needle 20. The rearward end of the needle 20 is preferably plugged so that fluid flowing through the needle flows through the side port 24 and into the flashback chamber 70. In the present instance, an adhesive plug such as epoxy is used to plug the rearward end of the needle. The forward end of the flashback chamber is closed by a porous vent plug 72. The vent plug 72 allows the passage of air out of the chamber 70, while preventing blood from escaping from the flashback chamber 70.

The needle 20 is biased rearwardly toward its retracted position by a biasing element 60. In the present instance, the biasing element is a spring 60 that surrounds the needle. The spring 60 is connected to the needle preferably by an adhesive, such as epoxy 62. The needle is releasably retained against the bias of the spring 60 by a needle retainer or lever arm 40 that is pivotally connected to the housing 30.

The needle retainer 40 has a forward portion 44 and a rearward portion 48. In the present instance, the forward portion 44 extends in the forward direction from a pivot 42, and the rearward portion 48 extends rearwardly from the pivot 42. The interior surface of the forward portion 44 of the retainer 40 abuts the hub 54 of the catheter 50 when the catheter is mounted on the insertion device 10. Preferably, the forward portion 44 of the retainer 40 abuts or engages the external surface of the catheter hub 54. Alternatively, the forward portion may engage the internal surface of the catheter hub 54. The rearward portion 48 of the needle retainer 40 is located rearwardly from the pivot point and catheter 50, when the catheter is mounted on the insertion device.

The rearward portion 48 of the needle retainer 40 functions as a release lever 41 having a latch 46 formed thereon. The lever 41 is pivotable between a locked position and an unlocked position. In the locked position, the release lever 41 extends generally parallel to the longitudinal axis of the device 10. The latch 46 on the end of the release lever 41 passes through an opening 32 in the side of the barrel 30, so that the rear end 26 of the needle 20 abuts the latch to retain the needle in its extended position.

The engagement between the forward portion 44 and the catheter hub 54 prevents the release lever 41 from pivoting to its unlocked position when the catheter is mounted on the insertion device. The rear portion 48 of the retainer 40 is preferably biased to pivot away from the side of the housing 30. After the catheter 50 is removed past the end of the lever 44, the retainer is free to pivot into its unlocked position, thus moving the latch 46 out of engagement with the rear end of the needle 20. The spring 60 then propels the needle rearwardly into the housing 30 to the position shown in FIGS. 2 and 4.

The catheter insertion device is initially provided in the configuration shown in FIG. 1. The operator of the catheter insertion device 10 first uses the needle point 22 to pierce a blood vessel of the patient. When the needle point 22 pierces the patient's blood vessel, blood flows through the needle 20 and through the port 24 of the needle. The blood emerges from the port 24 near the back end 26 of the needle 20 and collects in the transparent flashback chamber 70. The appearance of blood in the flashback chamber 70 serves as a visible indication to the operator that a blood vessel has been appropriately pierced, and that the catheter 50 is properly positioned. The operator then slides the catheter hub 54 off of the forward end of the device 10, in the direction of the pointed end 22 of the needle 20, to insert the catheter lumen 52 into the patient's blood vessel. This motion of removing the catheter hub 54 from the device causes the retainer 40 to automatically pivot out of contact with the end of the needle when the rim 55 of the catheter hub passes the end of lever 44. The needle is thereby released and withdrawn into the barrel 30 of the catheter insertion device 10 under the bias of spring 60. The operator need not perform any additional action to effectuate retraction of the needle other than that required by a normal catheter insertion procedure. The configuration of the used catheter insertion device 10 with the needle 20 retracted, is shown in FIG. 2. Thus, the needle is automatically retracted into the insertion device as the catheter is removed from the device in the usual manner.

Referring now to FIGS. 5-8, there is shown an alternate embodiment of a catheter insertion device 110. The alternate embodiment shown in FIGS. 58 incorporates elements that are similar to elements in the first embodiment described above in connection with FIGS. 1-4. Parts in FIGS. 5-8 that are similar to the parts in FIG. 1 are numbered by the same number designator with the addition of 100's thereto.

The catheter insertion device 110 includes an insertion needle 120 projecting forwardly from a barrel or housing 130. A cup-shaped sealing member 165 is positioned in the forward end or tip 134 of the housing 130 to provide a fluid-tight seal between the needle 120 and the housing. The needle 120 is releasably retained by a needle retainer 140 comprising a release lever 141. The needle retainer 140 engages a catheter 150 mounted on the tip 134 of the housing 130. In this manner, the catheter 150 impedes pivoting of the needle retainer 140 and prevents retraction of the needle 120 while the catheter is mounted on the housing 130 of the device 110.

The needle retainer 140 includes a forward portion 144 and a rearward portion 148. The forward portion 144 is forward of the pivot 142, and the rearward portion 148 is rearward of the pivot. In the embodiment of FIG. 5, the needle retainer is angled so that the forward portion 144 extends at an angle relative to the rearward portion 148. More specifically, the lever 140 forms an oblique angle about the pivot point so that the rear portion 148 is inclined or slanted into the housing 130 toward its latch end 146.

The housing 130 includes a gripping area that includes a plurality of longitudinally spaced ridges 166 projecting from the exterior surface of the housing 130. The housing 130 further includes a slot 167 formed along the gripping portion. The rearward portion 148 of the needle retainer 140 extends along the slot 167 and into the interior of the housing 130 as shown in FIG. 6. The arrangement of the slot 167 and the ridges 166 provide a guard to prevent the operator from contacting the rearward portion 148 of the needle retainer 140 during use of the device. In this manner, the operator is prevented from manually interfering with normal operation or separately controlling operation of the needle retainer 140.

The forward portion 144 of the needle retainer 140 includes an enlarged portion 145 that contacts the catheter hub 154 when the catheter 150 is mounted on the device, as shown in FIGS. 5 and 6. As shown in FIG. 8, the protrusion 145 is contoured to cooperate with the external surface of the tip 134 of the housing. In this arrangement, as shown in FIG. 7, when the catheter is removed, the protrusion 145 overlaps the tip, thereby increasing the distance that the needle retainer 140 is able to pivot.

As in the embodiment described above in connection with FIGS. 1-4, the catheter insertion device 110 in FIG. 5 is also operable to automatically retract the needle without manual intervention or requiring a separate step for retraction. The needle retainer 140 is biased toward an unlatched position, so that when the catheter 150 is removed from the insertion device 110, the needle retainer 140 automatically pivots into its unlatched position, releasing the needle 120. The spring 160 then propels the needle 120 rearwardly into the housing 130, so that the sharpened tip of the needle 120 is safely enclosed within the housing.

Referring to FIGS. 6 and 7, the tip 134 of the device and the needle retainer 140 are configured so that the forward end of the release lever 141 is rearward of the forward end of the tip. When the needle retainer 140 disengages the catheter hub 154, the catheter still overlaps the tip 134. In this way, the needle remains enclosed by the catheter 150 and the barrel 130 during and after retraction.

After the catheter has been inserted into the patient and the needle 120 has been retracted, the tip 134 of the device can be inserted into the catheter 150 to replug the catheter to prevent blood from leaking out of the catheter. For this reason, the catheter 150 and/or the forward end of the needle retainer 140 are configured to facilitate pivoting of the needle retainer so that the forward end of the needle retainer does not interfere with replugging of the catheter. Specifically, the forward edge of the enlarged portion 145 is rounded so that the forward portion 144 of the needle retainer 140 pivots downwardly from the perspective of FIG. 7 when the enlarged portion engages the rim 155 of the catheter 150. Alternatively, the rim 155 can be rounded or tapered, or the enlarged portion 145 can be tapered to facilitate pivoting of the needle retainer 140 upon forward axial displacement of the tip 134 relative to the catheter 150 after the catheter has been removed from the device a sufficient amount to disengage the needle retainer.

Referring now to FIGS. 9-10, there is shown a second alternative embodiment of a catheter insertion device 210. The device 210 incorporates elements that are similar to ones previously described. Such elements are designated with the same number designations with the addition of 200's thereto.

The catheter insertion device 210 includes an insertion needle 220 projecting forwardly from a barrel or housing 230. A cup-shaped seal member 265 is positioned in the forward end or tip 234 of the housing 230 to provide a fluid-tight seal between the needle 220 and the housing 230. The needle 220 is releasably retained by a pivotable needle retainer 240 comprising a release lever. One end of the needle retainer 240 engages a catheter 250 mounted on the tip 234 of the housing 230. In this arrangement, the catheter 250 impedes the needle retainer 240 from releasing the needle 220 while the catheter is mounted on the housing 230 under the retainer 240.

More specifically, the needle retainer 240 includes a forward portion 244 and a rearward portion 248. The forward portion 244 extends in the forward direction from a pivot point 242, and the rearward portion 248 extends rearwardly from the pivot 242. The housing includes a shroud 268 that encloses the rearward portion 248 of the needle retainer 240. The shroud 268 operates as a guard to prevent the operator from contacting the rearward portion 248 of the needle retainer 240 during use of the device. In this arrangement, the shroud 268 prevents the operator from manually preventing or controlling operation of the needle retainer 240 that automatically releases the needle for retraction, when the catheter is moved free of the forward portion 244 of the retainer 240.

In the embodiment in FIGS. 9 and 10, the rearward end 226 of the needle 220 is preferably bent transverse to the longitudinal axis of the needle. A latch 246 that is integral with the rearward portion 248 of the needle retainer projects into the interior of the housing 230. The latch 246 includes a groove 269 that engages the bent end 226 of the needle. Preferably the bent end 226 is bent at a predetermined orientation to the bevel angle of the needle tip. In this manner, the groove 269 in the latch 246 cooperates with the bent end 226 to maintain the bevel of the needle tip in a selected circumferential orientation when the needle is in the extended position.

Referring now to FIG. 11, there is shown a third alternate embodiment of a catheter insertion device 310. Elements of the device 310 that are similar to the corresponding elements of the embodiments discussed above are designated with the same reference numbers with the addition of 300's thereto.

The catheter insertion device 310 includes an insertion needle 320 projecting forwardly from a barrel or housing 330. A cup-shaped seal member 365 in the forward end or tip 334 of the housing 330 provides a fluid-tight seal between the needle 320 and the housing 330. The needle 320 is releasably retained by a needle retainer 340 comprising a release lever. The needle retainer 340 engages a catheter 350 mounted on the tip 334 of the housing 330. In this arrangement, the catheter 350 impedes the needle retainer 330 from releasing the needle 320 while the catheter is mounted on the housing 330.

The device 310 includes a needle retainer 340 having a forward portion 344 extending forwardly from a pivot 342, and a rearward portion 348 extending rearwardly from the pivot 342. As shown in FIG. 11, the forward and rearward portions of the retainer 340 are integrally formed.

The forward portion 344 includes a protuberance or detent 345 that cooperates with the catheter 350. More specifically, the catheter 350 includes a groove or recess 358 formed in the catheter hub 354 that cooperates with the detent 345 at the forward end of the needle retainer 340. When the catheter is mounted on the housing prior to use, the detent 345 is positioned forward of the recess 358. When the catheter is moved off of the device until the hub 354 is substantially, but not completely clear of the housing, the detent 345 engages the recess 358. The detent 345 and the recess 358 are configured to cooperate to produce a visual, audible and/or tactile signal for the operator when the detent engages the recess. In this arrangement, the recess 358 operates with the needle retainer 340 as a sensor for indicating to the operator that the catheter is about to be removed from the insertion device 310. After the signal from the sensor, continued forward displacement of the catheter 350 completely removes the catheter from the insertion device, causing retraction of the needle 320 into the housing. Hence, the signal produced between the detent 345 and recess 358 provides the operator with knowledge that continued removal of the catheter will cause retraction of the needle.

Referring now to FIGS. 12-18, a fourth alternate embodiment is illustrated. The embodiment in FIGS. 12-18 operates similarly to those embodiments illustrated in FIGS. 1-11. Elements of the device 410 that are similar to the corresponding elements of the embodiments discussed above are designated with the same reference numbers with the addition of 400's thereto.

This embodiment includes numerous advantageous features, such as the ability to adjust the length of needle that projects from the forward end of the catheter, the ability to align the bevel of the needle relative to the housing, an indicator for providing a audible, visual or tactile signal to the operator that continued forward removal of the catheter will cause retraction, and the ability to seal the catheter after needle retraction to reduce or eliminate blood leakage from the catheter after the catheter is inserted into the patient. The preferred embodiment also includes the feature of enclosing the needle during and after retraction of the needle so that the needle is not exposed after being inserted into the patient.

Referring now to FIGS. 12 and 16, the device 410 includes a barrel 430, a catheter 450 releasably mounted on the barrel, an insertion needle 420, and a needle retainer 440 releasably retaining the needle projecting forwardly from the barrel. The needle retainer 440 cooperates with the catheter, such that removing the catheter from the barrel 430 causes the needle retainer to disengage the needle. A spring 460 attached to the needle 420 then propels the needle rearwardly into the barrel 430.

The needle retainer 440 operates similarly to the needle retainer described above in connection with the previously described embodiments. The needle retainer pivots 440 about a pivot point 442, pivoting between a latched position and an unlatched position. In the latched position, the forward end of the needle retainer 440 engages the catheter 450, and a latch 446 at the rearward end of the needle retainer engages the needle 420. In this way, in the latched position, the needle retainer 440 retains the needle in an extended position against the bias of the spring 460, so that the pointed end 422 of the needle projects beyond the forward end of the catheter 450. When the catheter 450 is removed from the barrel 420, the needle retainer 440 pivots into the unlatched position. In the unlatched position, the needle retainer latch 446 disengages the needle 420 and the spring propels the needle rearwardly into the barrel 430.

The needle retainer 440 includes an elongated arm having a forward portion 444 extending forwardly of the pivot 442 and a rearward portion 448 extending rearwardly from the pivot. Referring to FIG. 17, the latch 446 is formed at the rearward end of the needle retainer 440. The latch 446 engages the rearward end of the needle 420 to releasably retain the needle.

The forward portion 444 of the needle retainer includes a detent 445 that cooperates with the catheter 450. More specifically, the catheter 450 includes a groove or recess 458 formed in the catheter hub 454 that cooperates with the detent 445 at the forward end of the needle retainer 440. When the catheter is mounted on the housing prior to use, the detent 445 is positioned forward of the recess 458. When the catheter is moved off of the device until the hub 454 is substantially, but not completely clear of the housing, the detent 445 engages the recess 458.

The detent 445 and the recess 458 are configured to cooperate to produce a visual, audible and/or tactile signal for the operator when the detent engages the recess. In this arrangement, the recess 458 operates with the needle retainer 440 as a sensor for indicating to the operator that the catheter is about to be removed from the insertion device 410. After the signal from the sensor, continued forward displacement of the catheter 450 completely removes the catheter from the insertion device, which actuates retraction of the needle 420 into the housing. Hence, the signal produced between the detent 445 and recess 458 provides the operator with knowledge that continued removal of the catheter will cause retraction of the needle.

The catheter 450 includes a flexible, elongated cannula 452 attached to the catheter hub 454. The cannula 452 telescopingly engages the needle so that the cannula sheaths the needle, with the sharpened tip of the needle 422 projecting beyond the forward end of the cannula. The rearward edge of the sharpened tip 422 is referred to as the heel of the needle bevel. The length of the needle between the heel of the needle bevel and the forward end of the cannula is referred to as the lie length. Preferably, the lie length is adjustable.

In the present instance, the lie length is adjustable by maintaining the extended position of the needle constant, and adjusting the position of the catheter 450 when the catheter is mounted on the barrel prior to use. The tip of the barrel 420 is adjustable to provide for adjustment of the catheter.

Referring now to FIG. 16, the barrel 420 includes a displaceable tip 434. In the present instance, the tip 434 is a separate component that is inserted into an opening at the forward end of the barrel 430. The tip 434 includes an external circumferential flange 439 against which the rearward edge 455 of the catheter hub 454 seats. Therefore, varying the axial position of the tip 434 adjusts the axial position of the flange 439 thereby adjusting the lie length.

The tip 434 includes a generally cylindrical rearward portion having an external diameter that is slightly less than the internal diameter of the forward portion of the barrel 430. A plurality of barbs 438 project from the external surface of rearward end of the tip 434. The barbs 430 engage the internal surface of the barrel 430 to connect the tip 434 to the barrel. The axial position of the flange 439 is determined by the distance that the rearward end of the tip is inserted into barrel 430. By adjusting the amount the tip is inserted, the axial position of the flange 439 is adjusted, thereby adjusting the lie length.

Referring to FIGS. 12-16, the tip 434 of the device and the needle retainer 440 are configured so that the forward end of the release lever is rearward of the forward end of the tip. When the needle retainer 440 disengages the catheter hub 454, the catheter still overlaps the tip 434. In this way, the needle remains enclosed by the catheter 450 and the barrel 430 during and after retraction.

Referring to FIG. 16, the tip 434 further includes a constricted portion 435 having an internal diameter slightly larger than the external diameter of the needle 420. The close fit between the constricted portion 435 and the needle limits leakage of blood into the barrel 430 during a replugging step, as described further below. In addition, an external circumferential rib 437 protrudes radially from the front end of the tip 434. The rib 437 cooperates with the internal cavity 451 of the catheter hub 454 to provide a fluid-tight seal. The internal cavity 451 is tapered, having a major diameter that is greater than the diameter of the rib 437 on the tip 434. Preferably, a substantially cylindrical zero draft zone 456 is formed at the forward-most portion of the internal cavity 451. The zero draft zone 456 has an internal diameter that is similar to the external diameter of the rib 437 on the tip 434. In this way, when the catheter 450 is mounted on the barrel 430, the rib 437 engages the zero draft zone 456 to form a fluid-tight seal.

Referring to FIG. 15, after the catheter has been inserted into the patient and the needle 420 has been retracted, the tip 434 of the device can be inserted into the catheter 450 to replug the catheter to prevent blood from leaking out of the catheter. For this reason, the catheter 450 and/or the forward end of the needle retainer 440 are configured to facilitate pivoting of the needle retainer so that the forward end of the needle retainer does not interfere with replugging of the catheter. Specifically, the forward edge of the enlarged portion 445 is tapered so that the forward portion 444 of the needle retainer 440 pivots downwardly from the perspective of FIGS. 14 and 15 when the enlarged portion engages the rim 455 of the catheter 450. Alternatively, the rim 455 can be rounded or tapered to facilitate pivoting of the needle retainer 440 upon forward axial displacement of the tip 434 relative to the catheter 450 after the catheter has been removed from the device a sufficient amount to disengage the needle retainer from the needle 420.

Referring to FIGS. 15-17, the catheter 450 is replugged after retraction by inserting the tip 434 of the barrel 430 into the catheter cavity 451 so that the circumferential rib 437 engages the zero draft zone 456. The rib 437 and the zero draft zone 456 cooperate to form a fluid-tight seal so that blood does not leak from the catheter around the tip 434.

In addition, the retracted needle 420 forms a seal with the constricted portion 435 of the tip 434 to reduce or eliminate blood leakage from the catheter 450 into the barrel 430. In the retracted position, the latch 446 deflects and/or deforms the needle as shown in FIG. 15.

It is desirable to align the sharpened tip 422 of the needle 420 so that the bevel of the sharpened tip is circumferentially located relative to the barrel 430, as illustrated in FIG. 12. Specifically, preferably, the sharpened tip is circumferentially located so that the forward-most point of the sharpened tip is vertically positioned below the heel of the tip bevel. In the present instance, the flashback chamber 470 is configured to cooperate with the ledge 449 of the needle retainer to facilitate aligning the bevel of the needle, as described below.

The flashback chamber 470 is generally cylindrical, and includes a flat surface extending along the length of the flashback chamber. The desired circumferential orientation of the needle bevel is located relative to the flat on the flashback chamber when the flashback chamber is connected to the needle. Referring to FIG. 17, the rearward portion 448 of the needle includes a generally planar surface or ledge 449 that cooperates with the flashback chamber 470 to circumferentially align the needle 420 relative to the barrel 430. As shown in FIGS. 12 and 17, when the needle retainer 440 is disposed in the latched position, the flat on the flashback chamber 470 is aligned with and engages the ledge 449 of the needle retainer. In this way, the flashback chamber 470 and the attached needle 420 are circumferentially located relative to the needle retainer, and in turn to the barrel 430.

The tip 434 further includes an external circumferential depression or recess 436. Initially, the catheter 450 encloses the tip 434 so that the operator cannot see the recess 436. As the operator removes the catheter 450 from the tip 434, the recess 436 is uncovered so that the operator can see the recess. After the recess 436 is uncovered, continued removal of the catheter 450 displaces the catheter beyond the enlarged forward end 445 of the needle retainer 440, so that the needle retainer pivots into the unlatched position, as shown in FIG. 16. In this way, the recess operates as a visual indicator to the operator, providing a visual signal that continued forward displacement of the catheter will cause needle retraction. Preferably, the recess 436 is textured to enhance the visual distinction between the recess and the rest of the external surface of the tip. Alternatively, a different visual indicator can be provided, such as a circumferential colored line located on the tip 434 axially rearwardly of the enlarged forward end 445 of the needle retainer 440.

Referring now to FIGS. 18-20, several design alternatives are shown that can be incorporated into one or more of the embodiments described above. For instance, in FIG. 18, recess 436' is shown axially aligned with the enlarged forward end 445' of the needle retainer 440'. In this alternative configuration, the recess 436' cooperates with the needle retainer to extend the pivot range of the needle retainer. The increased pivot range facilitates pivoting the latch 446' of the needle retainer radially outwardly beyond the flashback chamber 470' attached to the needle 420'.

FIG. 19 illustrates an alternate manner for connecting the needle and the needle retainer. In the previously described embodiments, the needle retainer engages the rearward end of the needle. In FIG. 19 the latch 446" of the needle retainer 440" engages the flashback chamber 470", which is connected to the rearward end of the needle 420". In such a configuration, the needle 420" need not include a side port. Instead, the rearward end of the needle communicates with an opening at the forward end of the flashback chamber.

FIG. 20 illustrates yet another alternative for retaining the needle. In FIG. 20, the needle retainer latch includes a plurality of serrated teeth 546. The serrated teeth 546 on the needle retainer 540 cooperate with a mating set of serrated teeth formed on the exterior of the flashback chamber 570. The flashback chamber 570 abuts the rearward end of the needle 520, so that the needle is retained in an extended position when the needle retainer 540 engages the flashback chamber. In the present instance, the flashback chamber is not attached to the needle 520, so that the flashback chamber dissociates from the needle after the needle is retracted. The mating serrations also provide a mechanism for adjusting the needle relative to the catheter 550 during assembly, for adjusting the needle lie.

Figure 21:
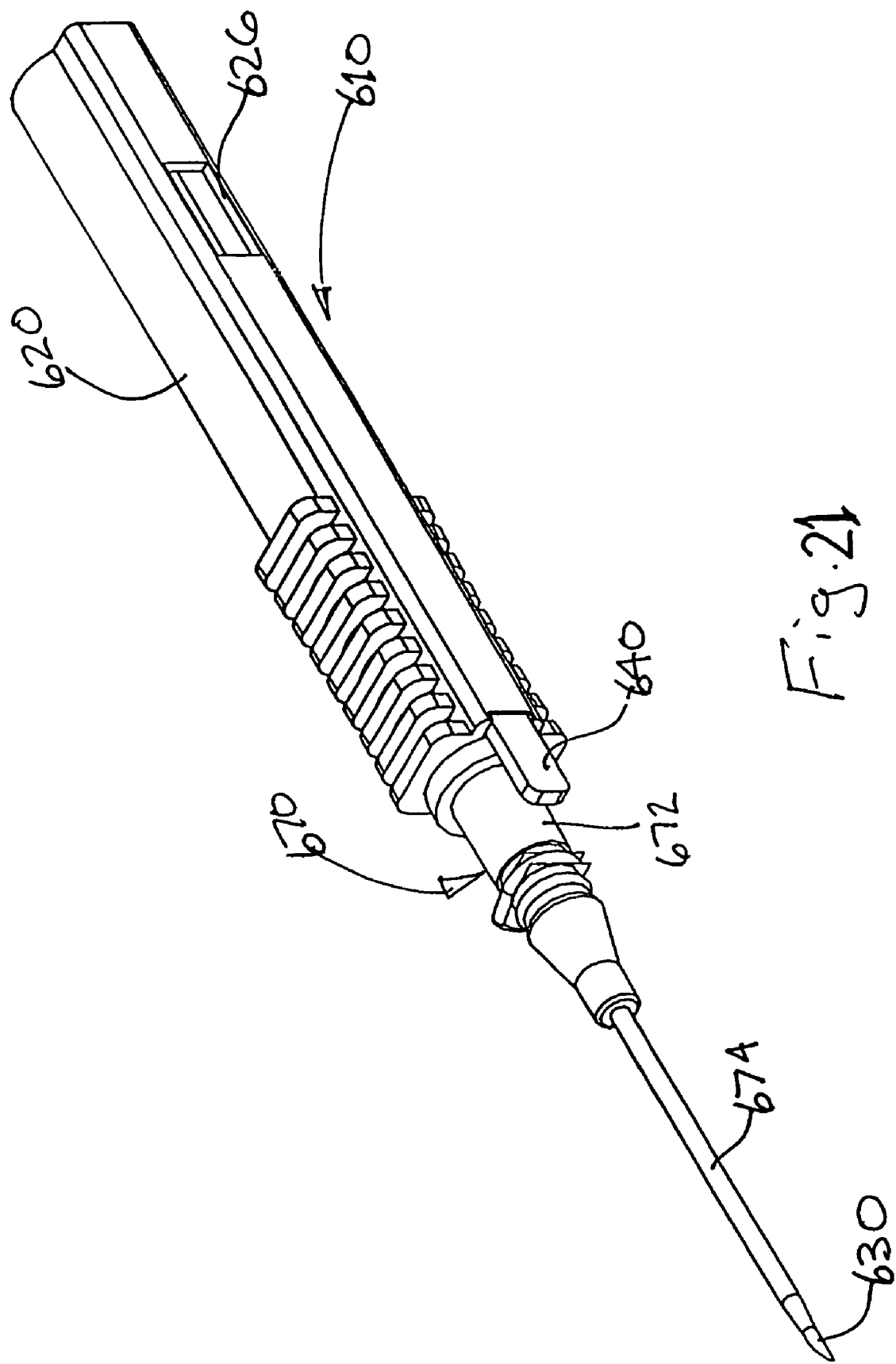
FIG. 21 is a perspective view of a fifth alternate embodiment of a catheter insertion device having a retractable needle.

Referring now to the FIGS. 21-24 in general and to FIG. 21 specifically, a fifth alternate embodiment of a device for inserting an over-the needle catheter 670 into a patient is designated generally 610. The device 610 includes a retractable needle 630 for piercing the skin of the patient to insert the catheter 670. After the catheter 670 is inserted into the patient, the needle 630 automatically retracts into the device 610 so that the sharpened tip of the contaminated needle is enclosed within the device to prevent inadvertent needle sticks.

Figures 22, 23, 24:
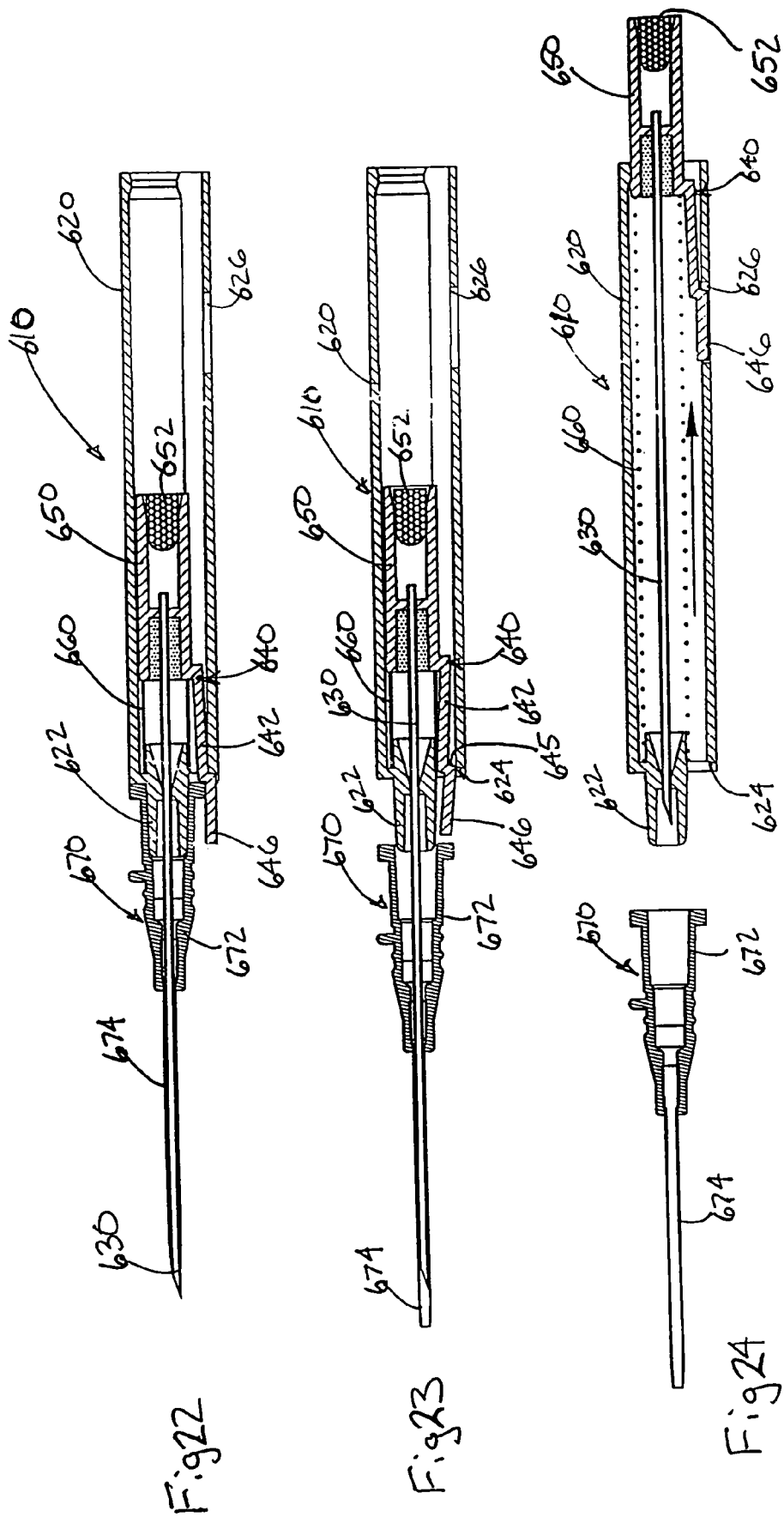
FIG. 22 is a cross-sectional view of the device shown in FIG. 21.
FIG. 23 is a cross-sectional view of the device shown in FIG. 22, illustrating the device with the catheter removed prior to retraction of the needle.
FIG. 24 is a cross-sectional view of the device shown in FIG. 22, illustrating the device after retraction of the needle.

Referring to FIGS. 22-24, the device includes a generally cylindrical housing 620, the needle 630, a spring 660 biasing the needle rearwardly, and a needle retainer 640 releasably retaining the needle against the bias of the spring. The needle is operable between two positions, a projecting position and a retracted position. In the projecting position, the needle 630 projects forwardly from the forward end of the housing 620. In the retracted position, the needle is retracted into the housing so that the sharpened tip is enclosed within the housing to prevent inadvertent contact with the sharpened tip. When the needle is in the projecting position, as shown in FIG. 22, the spring biases the needle rearwardly toward the retracted position. The needle retainer releasably retains the needle in the projecting position, against the bias of the spring. The needle retainer cooperates with the catheter 670, so that when the catheter is removed from the device the needle retainer automatically releases the needle and the needle retracts into the housing, as shown in FIG. 24.

Referring now to FIG. 22, the elements of the device 610 will be described in greater detail. The housing is generally cylindrical and the forward end of the housing 620 has a reduced diameter tapered nose 622. The catheter 670 is mounted on the nose 622. Accordingly, the nose 622 is tapered to cooperate with the internal taper of the hub 672 of the catheter 670.

The catheter 670 includes a generally conical hub 672 and a flexible cannula 674 fixedly connected to the catheter hub. The catheter 670 is mounted on the nose 622 of the housing so that the cannula 674 sheaths the forward end of the needle. However, the sharpened tip of the needle projects forwardly from the cannula so that the sharpened tip is exposed prior to use.

When the catheter 670 is mounted on the nose 622, the catheter hub 672 engages the needle retainer 640. The needle retainer 640 is an elongated arm fixedly connected with the needle 630. The arm projects forwardly through an opening in the forward end of the housing, adjacent the tip. The forward portion of the arm 640 forms a follower portion 646. The follower portion projects forwardly from the housing, through the opening in the housing adjacent the nose 622 and engages the catheter hub 672.

The needle retainer 640 includes a ridge 645 that protrudes radially outwardly, rearwardly of the follower portion 646. The ridge 645 engages a lip 624 formed by the opening through which the arm 640 projects adjacent the nose. The ridge 645 operates as a latch to retain the needle retainer and the attached needle against the bias of the spring.

When the catheter 670 is mounted on the nose 622, the catheter hub 672 engages the follower portion 646 of the needle retainer 640 so that the ridge 645 is wedged into engagement with the lip 624. In this way, when the catheter is mounted on the device, the needle 630 is maintained in the projecting position against the bias of the needle. Removing the catheter 670 allows the needle retainer to deflect radially inwardly disengaging the ridge from the lip. In the present instance, the rearward bias of the spring radially deflects the needle retainer when the catheter is removed.

The needle retainer arm is formed of a flexible plastic so that the arm is resiliently deformable. In its relaxed state, the needle retainer arm 640 is disposed into engagement with the lip 624 of the forward opening. Preferably, the lip 624 is tapered rearwardly and the ridge 645 on the needle retainer 640 forms a matingly tapered surface. These mating surfaces can be seen most clearly in FIGS. 23 and 24. Configured in this way, the rearward axial biasing force of the spring acts upon the arm in the form of a radial force component and an axial force component. The radial force component urges the needle retainer arm 640 inwardly so that the ridge 645 rides up and over the lip 624 until the ridge is out of engagement with the lip. The spring 660 then propels the needle retainer and the attached needle rearwardly into the housing so that the sharpened tip of the needle is enclosed within the housing.

The device 610 further includes a fluid reservoir 650 attached to the rearward end of the needle, enclosing the rearward end of the needle. The fluid reservoir 650 is in fluid communication with the needle 630 and operates as a flashback chamber. Accordingly, when the needle is inserted into a patient's vein, blood flows through the needle into the flashback chamber. The rearward end of the flashback chamber 650 is sealed by a porous hydrophobic vent plug 652. Air passes though the vent plug to allow air to pass out of the flashback chamber when the blood enters the flashback chamber. However, the vent plug 652 is not permeable to blood to prevent blood from leaking out of the flashback chamber. The housing and the flashback chamber are formed of translucent plastic so that the blood in the flashback chamber serves as a visible indicator that the needle is properly inserted into the patient's vein.

In the present instance, the flashback chamber 650 and the needle retainer 640 are integrally formed as a unitary structure. The two elements are fixedly attached to the needle by an adhesive such as UV curable epoxy. The spring is disposed within the housing, circumscribing the needle. The forward end of the spring bears against the forward end of the housing, the other end of the spring bears against the integral needle retainer and flashback chamber.

In the present instance, the housing 620 is shorter than the combined length of the needle 630 and the flashback chamber 650. Accordingly, the rearward end of the housing 620 is generally open, allowing the flashback chamber to project rearwardly out of the housing when the needle is retracted, as shown in FIG. 24. The device also includes a locking or limiting feature to ensure that the needle is not propelled rearwardly out of the housing. Preferably, an aperture 626 sized to receive the forward portion 646 of the needle retainer arm 640 is formed in the side of the housing to operate as the rearward lock. The resilience of the needle retainer biases the needle retainer radially outwardly. When the needle is propelled rearwardly, the forward end of the needle retainer 646 engages the aperture 626 so that the ridge 645 engages the rearward edge of the aperture, retaining the needle against continued rearward displacement. In addition, the forward end of the needle retainer 640 engages the forward edge of the aperture 626 to retain the needle against forward displacement, so that the needle cannot be reextended after it is retracted.

When the catheter 670 is removed from the device and inserted into a patient, blood from the patient may flow out the rearward end of the catheter. Typically, once the catheter is attached to a fluid reservoir, such as an IV bag, the fluid pressure from fluid in the IV bag is sufficient to prevent or limit the flow of blood from the patient through the catheter. However, until the IV bag is connected to the catheter, blood may leak out the catheter. Therefore, it may be desirable to plug the catheter to prevent blood leakage after the catheter is inserted into a patient.

Accordingly, preferably, the nose 622 forms a fluid-tight seal with the interior of the catheter hub 672 when the catheter is mounted on the nose. In this way, after the catheter is removed from the housing and the needle is retracted, the nose can be inserted into the catheter to plug the catheter. Further, referring to FIG. 23, preferably the nose extends forward of the follower portion 646 of the needle retainer 640 so that the nose 622 substantially plugs the catheter immediately after the needle is retracted. In addition, since the nose 622 projects forward of the follower portion 646, the needle is never exposed during and after retraction.

Configured as described above, the device operates as follows. Prior to use, the needle 630 is disposed in the projecting position so that the sharpened tip of the needle is exposed. The sharpened tip of the needle is inserted into a vein of a patient. Blood flowing into the flashback chamber 650 indicates to the medical professional that the needle is inserted into a vein. The catheter 670 is then threaded into the patient's vein by advancing the catheter to remove the catheter from the device 610. For this purpose, preferably, the catheter hub 672 includes a protrusion 673 that the medical professional can push forward with one of the fingers of the hand holding the device. When the catheter is advanced forward of the follower portion 646 of the needle retainer 640, the needle retainer 640 deflects inwardly so that the needle is released. The spring 660 then propels the needle 630, the needle retainer 640 and the flashback chamber 650 rearwardly so that the sharpened tip of the needle is enclosed within the housing 620. If the medical profession desires to do so, the nose 622 can then be inserted into the catheter to replug the catheter to prevent blood leakage.

Referring now to FIGS. 25-27, a sixth alternative embodiment is illustrated. Elements in the sixth alternate embodiment that are similar to elements of the prior embodiment illustrated in FIGS. 21-24 and described above are designated with like reference numbers, with the addition of 700's thereto.

This embodiment is designated generally 710. The device 710 includes a housing 720, a retractable needle 730, a spring 760 biasing the needle rearwardly, and a needle retainer 740 releasably retaining the needle against the bias of the spring. An over-the-needle catheter 770 is mounted on the forward end of the device 710. The needle retainer 740 cooperates with the catheter so that upon removing the catheter from the device 710, the needle is released, and the spring propels the needle rearwardly into the housing 720.

The needle retainer 740 is configured similarly to the needle retainer 640 described in the previous embodiment. The needle retainer 740 comprises an elongated resiliently flexible arm fixedly connected with the needle 730. The forward end of the needle retainer projects through an opening at the forward end of the housing adjacent the tip 722. The forward portion 746 of the needle retainer engages the side of the catheter hub 772. Similar to the previous embodiment, the catheter hub 772 wedges the needle retainer arm radially outwardly so that a ridge 745 on the arm engages a lip 724 formed by the opening at the forward end of the housing. Accordingly, when the catheter 770 is removed from the device 710, the needle retainer 740 deflects inwardly to release the needle 730. The spring then propels the needle rearwardly into the housing 720. As shown in FIG. 27, the housing is elongated so that the entire length of the needle and the flashback chamber is enclosed within the housing in the retracted position.

In this way, as with the previous embodiment, the needle automatically retracts after use so that the medical professional need not perform any additional steps to ensure that the contaminated needle is safely enclosed. The step of inserting the catheter 770 into the patient is sufficient to effectuate retraction. However, as discussed further below, the medical professional may delay retraction if desired.

It may be desirable to allow the medical professional to delay retraction after the catheter is inserted into the patient. Therefore, the device 710 may include a window 721 in the side of the housing 720. The needle retainer 740 is disposed adjacent the window allowing the medical professional to manually engage the needle retainer. If the medical professional desires to control retraction, the medical professional can apply pressure to deflect the needle retainer radially inwardly so that the retainer abuts an interior wall. In this way, the needle retainer is pinched between the grip of the medical professional and the interior wall to prevent the needle from retracting into the housing. Once the medical professional releases the needle retainer, the needle retracts into the housing.

Preferably, the window 721 is located so that the medical professional engages the needle retainer when grasping the device 710 for use. For this reason, preferably, a gripping portion is formed at the forward end of the housing. The gripping portion is formed by a pair of opposing concavely curved surfaces along the sides of the housing. The window 721 is formed in one of the opposing curved surfaces of the gripping portion.

The device operates as follows. Prior to use, the needle projects forwardly from the housing as shown in FIG. 25. The medical professional grasps the gripping portion of the housing to hold the device 710. In doing so, the medical professional engages the needle retainer through the window 721. The needle 730 is inserted intravenously into a patient. Once blood flow is detected in the flashback chamber 750, the catheter is axially advanced to insert the catheter into the patient. Once the catheter is axially advanced forward of the needle retainer, the needle is freed to retract except for the force being applied to the needle retainer by the medical professional. If the medical professional does not want to delay retraction, the medical professional can release the finger pressure on the needle retainer so that the bias of the spring overcomes the finger pressure. Alternatively, the medical professional can delay retraction by maintaining his or her grip with sufficient force to overcome the bias of the spring 760. Once the medical professional releases the device, the needle automatically retracts into the housing so that the sharpened tip of the housing is enclosed. In this way, the needle automatically retracts after the device is used, and without any additional step, such as depressing a button. At the same time, if the medical professional desires to control retraction by delaying retraction, he or she may do so, without performing any additional steps. The natural steps of using the device allow such control. However, even if the medical professional desires to delay the retraction, the needle will eventually automatically retract without any further operation once the medical professional releases his or her grip on the device.

The device 710 also includes an adjustable nose piece 722. In the previous embodiment, the nose 722 is integrally formed with the housing. In this embodiment, the nose is a separate piece that is inserted into a socket at the forward end of the housing that is formed to receive the nose piece. The nose piece 722 may be axially adjusted relative to the housing 720. By adjusting the axial position of the nose piece, the length of the exposed sharpened needle tip projecting from the catheter cannula can be varied.

Referring now to FIGS. 28-32 in general and to FIG. 28 specifically, there is shown a seventh alternate embodiment of a catheter insertion device 810 for inserting a catheter 850 into a patient. The device 810 has a needle 820 to guide the catheter 850 into a vessel of the patient. The insertion device 810 is adapted to automatically retract the needle 820 inside the insertion device 810 when the operator removes the catheter 850 from the device. In addition, the device is configured to allow the operator to delay the retraction. These features allow the operator to control retraction, while ensuring that the needle automatically retracts after use to render the needle non-reusable and safely disposable.

The catheter insertion device 810 includes a generally cylindrical hollow barrel or housing 830 having a reduced diameter forward tip portion 834. The needle 820 is releasably retained so that the forward end of the needle projects forwardly through a hole in the barrel tip 834. The needle is operable between an extended position and a retracted position. In the retracted position, the needle is enclosed within the housing.

The catheter 850 is initially mounted on the forward end of the catheter insertion device 810 with the needle 820 projecting from the front of the device through the catheter. The catheter 850 comprises a cannula 852 and a hub 854. The cannula 852 sheaths or receives the front portion of needle 820, so that the sharpened point of the needle extends slightly beyond the open end of the cannula.

The catheter 850 includes a flexible, elongated cannula 852 attached to the catheter hub 854. The cannula 852 telescopingly engages the needle so that the cannula sheaths the needle, with the sharpened tip of the needle 822 projecting beyond the forward end of the cannula. The rearward edge of the sharpened tip 822 is referred to as the heel of the needle bevel. The length of the needle between the heel of the needle bevel and the forward end of the cannula is referred to as the lie length. Preferably, the lie length is adjustable.

In the present instance, the lie length is adjustable by maintaining the extended position of the needle constant, and adjusting the position of the catheter 850 when the catheter is mounted on the barrel prior to use. The tip of the barrel 820 is adjustable to provide for adjustment of the catheter.

Referring now to FIG. 30, the barrel 820 includes a displaceable tip 834. In the present instance, the tip 834 is a separate component that is inserted into an opening at the forward end of the barrel 830. The tip 834 includes an external circumferential flange 839 against which the rearward edge 855 of the catheter hub 854 seats. Therefore, varying the axial position of the tip 834 adjusts the axial position of the flange 839 thereby adjusting the lie length.

The tip 834 includes a generally cylindrical rearward portion having an external diameter that is slightly less than the internal diameter of the forward portion of the barrel 830. A plurality of barbs 838 project from the external surface of rearward end of the tip 834. The barbs 838 engage the internal surface of the barrel 830 to connect the tip 834 to the barrel.

The axial position of the flange 839 is determined by the distance that the rearward end of the tip is inserted into barrel 830. By adjusting the amount the tip is inserted, the axial position of the flange 839 is adjusted, thereby adjusting the lie length.

As shown in FIG. 30, a generally cylindrical chamber 870 is attached to the rearward end of the needle. The chamber 870 forms a flashback chamber. The flashback chamber 870 is attached to the rearward end of the needle 820 so that the flashback chamber encloses the rearward end of the needle 820. The rearward end of the flashback chamber is closed by a porous vent plug 872. The vent plug 872 allows the passage of air out of the chamber 870, while preventing blood from escaping from the flashback chamber 870.

The needle 820 is biased rearwardly toward its retracted position by a biasing element 860. In the present instance, the biasing element is a coil spring 860 that surrounds the needle. The forward end of the spring 860 bears against an internal shoulder formed in the tip 834. The rearward end of the spring bears against the flashback chamber 870, biasing the flashback chamber and the attached needle rearwardly. Alternatively, the spring 860 may be connected to the needle by an adhesive, such as epoxy. The needle 820 and flashback chamber 870 are releasably retained against the bias of the spring 860 by a needle retainer or lever arm 840 that is pivotally connected to the housing 830.

The needle retainer 840 has a forward portion 844 and a rearward portion 848. In the present instance, the forward portion 844 extends in the forward direction from a pivot 842, and the rearward portion 848 extends rearwardly from the pivot 842. The interior surface of the forward portion 844 of the retainer 840 abuts with the hub 854 of the catheter 850 when the catheter is mounted on the insertion device 810. Preferably, the forward portion 844 of the retainer 840 abuts or engages the external surface of the catheter hub 854. Alternatively, the forward portion may engage the internal surface of the catheter hub 854. The rearward portion 848 of the needle retainer 840 is located rearwardly from the pivot point and catheter 850, when the catheter is mounted on the insertion device.

The rearward portion 848 of the needle retainer 840 comprises a release lever having a latch 846 formed thereon. The lever is pivotable between a locked position and an unlocked position. In the locked position, the release lever extends generally parallel to the longitudinal axis of the device 810. The latch 846 on the end of the release lever passes through an opening 832 in the side of the barrel 830, so that the rear end of the flashback chamber 870 abuts the latch to retain the needle in its extended position.

It is desirable to align the sharpened tip 822 of the needle 820 so that the bevel of the sharpened tip is circumferentially located relative to the barrel 830, as illustrated in FIG. 28. Specifically, preferably, the sharpened tip is circumferentially located so that the forward-most point of the sharpened tip is vertically positioned below the heel of the tip bevel. In the present instance, the flashback chamber 870 is configured to cooperate with needle retainer to facilitate aligning the bevel of the needle, as described below.

The flashback chamber 870 is generally cylindrical, and includes a flat surface extending along the length of the flashback chamber. The desired circumferential orientation of the needle bevel is located relative to the flat on the flashback chamber when the flashback chamber is connected to the needle. Referring to FIG. 30, the rearward portion 848 of the needle retainer includes a generally planar surface or ledge 849 that cooperates with the flashback chamber 870 to circumferentially align the needle 820 relative to the barrel 830.

As shown in FIG. 30, when the needle retainer 840 is disposed in the latched position, the flat on the flashback chamber 870 is aligned with and engages the ledge 849 of the needle retainer. In this way, the flashback chamber 870 and the attached needle 820 are circumferentially located relative to the needle retainer, and in turn to the barrel 830.

The engagement between the forward portion 844 of the needle retainer lever and the catheter hub 854 prevents the lever from pivoting to its unlocked position when the catheter is mounted on the insertion device. The rear portion 848 of the retainer 840 is preferably biased to pivot away from the side of the housing 830. In the present instance, the face of the latch 846 that engages the flashback chamber 870 is angled so that a portion of the rearward bias of spring 860 is transferred to the lever biasing the lever radially outwardly. After the catheter 850 is removed past the end of the lever, the retainer is free to pivot into its unlocked position, thus moving the latch 846 out of engagement with the rear end of the needle 820. The spring 860 then propels the needle rearwardly into the housing 830.

The operator can control retraction of the needle, if desired, as follows. The needle retainer 840 includes a rib 845 that is transverse the longitudinal axis of the needle retainer lever. As shown in FIGS. 28 and 29, the barrel 830 includes a gripping portion comprised of a plurality of parallel spaced apart ribs 831. The needle retainer rib 845 is generally parallel to the gripping ribs 831 so that the needle retainer rib 845 forms part of the gripping portion. In this way, if the operator desires to control retraction of the needle, the operator grasps the rib 845 of the needle retainer when grasping the gripping portion of the device 810.

By grasping the needle retainer rib 845, the operator impedes pivoting of the needle retainer 840 from the locked position to the unlocked position. After the operator inserts the catheter 850 into the patient, the forward portion 844 of the needle retainer is disengaged from the catheter, thereby allowing the needle retainer to pivot toward the unlocked position. However, the operator's grasp of the needle retainer rib 845 operates as an override preventing the needle retainer from pivoting into the unlocked position. The operator can control retraction by maintaining an inward force on the needle retainer rib 845 until retraction is desired. Once the operator releases the needle retain rib 845 after the catheter 850 has been disengaged from the needle retainer 840, the needle retainer is free to pivot into the unlocked position so that the spring 860 propels the needle 820 rearwardly into the barrel 830. In this way, the device prevents retraction from occurring until after the catheter 850 is disengaged from the housing of the insertion device. In addition, the device allows the operator to control the timing of retraction, while ensuring that retraction occurs after use of the device.

The catheter insertion device is initially provided in the configuration shown in FIG. 28. The operator of the catheter insertion device 810 first uses the needle point 822 to pierce a blood vessel of the patient. When the needle point 822 pierces the patient's blood vessel, blood flows through the needle 820 and collects in the transparent flashback chamber 870. The appearance of blood in the flashback chamber 870 serves as a visible indication to the operator that a blood vessel has been appropriately pierced, and that the catheter 850 is properly positioned. The operator then slides the catheter hub 854 off of the forward end of the device 810, in the direction of the pointed end 822 of the needle 820, to insert the catheter lumen 852 into the patient's blood vessel. This motion of removing the catheter hub 854 from the device causes the retainer 840 to automatically pivot out of contact with the end of the needle when the rim 855 of the catheter hub passes the end of lever 844. However, the operator can temporarily override the automatic retraction by grasping the needle retainer rib 845 prior to removing the catheter hub. Once the operator releases the needle retainer rib 845, the needle retainer pivots out of engagement with the needle 820. The needle is thereby released and withdrawn into the barrel 830 of the catheter insertion device 810 under the bias of spring 860. The operator need not perform any additional action to effectuate retraction of the needle other than that required by a normal catheter insertion procedure. At the same time, the operator can intervene to delay retraction, if desired.

Referring to FIG. 30, preferably the tip 834 further includes a constricted portion 835 having an internal diameter slightly larger than the external diameter of the needle 820. The close fit between the constricted portion 835 and the needle limits leakage of blood into the barrel 830 during a replugging step, as described further below. In addition, an external circumferential rib 837 protrudes radially from the front end of the tip 834. The rib 837 cooperates with the internal cavity of the catheter hub 854 to provide a fluid-tight seal. The internal cavity is tapered, having a major diameter that is greater than the diameter of the rib 837 on the tip 834. Preferably, a substantially cylindrical zero draft zone is formed at the forwardmost portion of the internal cavity. The zero draft zone has an internal diameter that is similar to the external diameter of the rib 837 on the tip 834. In this way, when the catheter 850 is mounted on the barrel 830, the rib 837 engages the zero draft zone to form a fluid-tight seal.

After the catheter has been inserted into the patient and the needle 820 has been retracted, the tip 834 of the device can be inserted into the catheter 850 to replug the catheter to prevent blood from leaking out of the catheter. For this reason, the catheter 850 and/or the forward end of the needle retainer 840 are configured to facilitate pivoting of the needle retainer so that the forward end of the needle retainer does not interfere with replugging of the catheter. Specifically, the forward edge of the needle retainer is rounded so that the forward portion 844 of the needle retainer 840 pivots downwardly from the perspective of FIGS. 28 and 30 when the needle retainer engages the rim 855 of the catheter 850. Alternatively, the rim 855 can be rounded or tapered to facilitate pivoting of the needle retainer 840 upon forward axial displacement of the tip 834 relative to the catheter 850 after the catheter has been removed from the device a sufficient amount to disengage the needle retainer from the needle 820.

The catheter 850 is replugged after retraction by inserting the tip 834 of the barrel 830 into the catheter cavity so that the circumferential rib 837 engages the zero draft zone. The rib 837 and the zero draft zone cooperate to form a fluid-tight seal so that blood does not leak from the catheter around the tip 834. In addition, the retracted needle 820 forms a seal with the constricted portion 835 of the tip 434 to reduce or eliminate blood leakage from the catheter 850 into the barrel 830. In the retracted position, the latch 846 deflects and/or deforms the needle. Although the device has been described as including structure for replugging the catheter after insertion, it may be desirable to eliminate the replugging feature.

The tip 834 further includes an external circumferential depression or recess 836. Initially, the catheter 850 encloses the tip 834 so that the operator cannot see the recess 836. As the operator removes the catheter 850 from the tip 834, the recess 836 is uncovered so that the operator can see the recess. After the recess 836 is uncovered, continued removal of the catheter 850 displaces the catheter beyond the forward end of the needle retainer 840, so that the needle retainer pivots into the unlatched position. In this way, the recess operates as a visual indicator to the operator, providing a visual signal that continued forward displacement of the catheter will cause needle retraction. Preferably, the recess 836 is textured to enhance the visual distinction between the recess and the rest of the external surface of the tip. Alternatively, a different visual indicator can be provided, such as a circumferential colored line located on the tip 834 axially rearwardly of the forward end of the needle retainer 840.

Referring now to FIGS. 33-36, there is shown an eighth alternate embodiment of a catheter insertion device 910. The alternate embodiment shown in FIGS. 33-36 incorporates elements that are similar to elements in the embodiment described above in connection with FIGS. 28-32. Parts in FIGS. 33-36 that are similar to the parts in FIGS. 28-32 are numbered by the same number designator with the addition of 900's thereto.

The catheter insertion device 910 includes an insertion needle 920 projecting forwardly from a barrel or housing 930. The needle 920 is releasably retained by a needle retainer 940 comprising a release lever. The needle retainer 940 engages a catheter 950 mounted on the tip 934 of the housing 930. In this manner, the catheter 950 impedes pivoting of the needle retainer 940 and prevents retraction of the needle 920 while the catheter is mounted on the housing 930 of the device 910.

As in the embodiment described above in connection with FIGS. 28-32, the catheter insertion device 910 in FIG. 33 is also operable to automatically retract the needle without manual intervention or requiring a separate step for retraction. The needle retainer 940 is biased toward an unlatched position, so that when the catheter 950 is removed from the insertion device 910, the needle retainer 940 automatically pivots into its unlatched position, releasing the needle 920. The spring 960 then propels the needle 920 rearwardly into the housing 930, so that the sharpened tip of the needle 920 is safely enclosed within the housing.

In addition, as in the previous embodiment, the device 910 includes an exposed, manually actuable surface that allows the operator to intervene to delay retraction if desired. Specifically, the device includes a control button 980 that engages a pawl 949 connected to the needle retainer 940. The control button 980 operates between a locked position and an unlocked position. In the locked position the control button engages the pawl 949 on the needle retainer 940 preventing the needle retainer from pivoting into the unlatched position to release the needle 920. The control button is displaceable toward the unlocked position, which corresponds to the needle retainer 940 being in the unlatched position.

The control button 980 and pawl 949 have mating tapered surfaces. When the needle retainer 940 pivots, the mating tapered surfaces of the pawl and control button transfers a vertical force to the button, displacing the control button upwardly into the unlocked position. Accordingly, absent operator intervention, when the catheter 950 is removed from the housing 930, the needle retainer 940 pivots into the unlatched position, displacing the control button into the unlocked position. The needle then retracts into the housing.

The operator can intervene to delay retraction by depressing the control button 980 before the catheter is removed. The downward force applied by the operator on the control button locks the pawl 949 in place, preventing the needle retainer from pivoting. After the catheter is removed from the housing, the needle retainer retains the needle as long as the operator depresses the control button. As soon as the operator releases the control button, the pawl is free to rotate, so that the needle retainer pivots into the unlatched position and the needle retracts. In this way, retraction of the insertion needle occurs automatically after the device is used, but the operator can delay retraction if desired.

The device 910 also illustrates an alternate arrangement for the flashback chamber 920. The flashback chamber 920 can be configured as in the previous embodiment in which the flashback chamber 870 encloses the rearward open end of the needle 820, and the needle retainer 840 engages the flashback chamber. Alternatively, in the present embodiment, the rearward end of the needle 920 projects rearwardly from the flashback chamber 970, and the needle retainer 940 engages the rearward end of the needle. The rearward end of the needle is plugged to prevent blood from leaking into the housing. In addition, a side port is formed in the side of the needle, and the flashback chamber encloses the side port. Blood from the patient flows through the side port and into the flashback chamber, serving as a visual indicator that the patient's artery has been pierced.

Referring now to FIGS. 37-40, there is shown a ninth alternative embodiment of a catheter insertion device 1010. The device 1010 incorporates elements that are similar to devices previously described and illustrated in FIGS. 28-36. Such elements are designated with the same number designations with the addition of 1000's thereto.

The catheter insertion device 1010 includes an insertion needle 1020 projecting forwardly from a barrel or housing 1030. The needle 1020 is releasably retained by a pivotable needle retainer 1040 comprising a release lever. One end of the needle retainer 1040 engages a catheter 1050 mounted on the tip 1034 of the housing 1030. In this arrangement, the catheter 1050 impedes the needle retainer 1040 from releasing the needle 1020 while the catheter is mounted on the housing 1030 under the retainer 1040.

As in the embodiments described above in connection with FIGS. 2836, the catheter insertion device 1010 in FIG. 37 is also operable to automatically retract the needle without manual intervention or requiring a separate step for retraction. The needle retainer 1040 is biased toward an unlatched position, so that when the catheter 1050 is removed from the insertion device 1010, the needle retainer 1040 automatically pivots into its unlatched position, releasing the needle 1020. The spring 1060 then propels the needle 1020 rearwardly into the housing 1030, so that the sharpened tip of the needle 1020 is safely enclosed within the housing.

In addition, as in the previously described embodiments, the device 1010 includes an exposed, manually actuable surface that allows the operator to intervene to delay retraction if desired. Specifically, the housing includes a gripping portion 1091 providing a surface for the operator to grasp the device 1010. The needle retainer 1040 is located adjacent the gripping portion 1031 so that the operator can readily engage the needle retainer to prevent the needle retainer from pivoting into the unlatched position.

Referring to FIGS. 37 and 38, the housing 1030 includes the gripping portion 1031, which is formed of a plurality of parallel spaced apart ribs. The ribs form a convex curved surface providing a secure anti-slip surface. As shown in FIG. 37, the housing may include opposing gripping surface for gripping the device. In the present instance, the barrel includes the gripping portion 1031 on one side of the housing, and the rearward portion 1048 of the needle retainer 1040 is located on the other side of the housing, opposing the gripping portion. The exposed surface of the rearward portion 1048 of the needle retainer 1040 is configured and textured similar to the gripping portion 1031. Accordingly, when the operator grasps the device for use, the operator's normal grip on the device operates to depress the rearward portion of the needle retainer. As long as the operator depresses the rearward portion of the needle retainer, the operator prevents the needle retainer from pivoting radially outwardly to release the needle for retraction.

The device 1010 also includes a telescoping barrel to reduce the overall length of the housing prior to use. Alternatively, the device 1010 can use a single piece housing as described in one of the foregoing devices 810 described above.

The housing 1030 of the device 1010 comprises two components, an outer sleeve 1090 and an inner sleeve 1095. The inner sleeve 1095 telescopes within the outer sleeve 1090. Prior to use, the inner sleeve 1095 is enclosed within the rearward end of the outer sleeve 1090. When the needle 1020 is retracted, the flashback chamber 1070 and attached needle engages the inner sleeve, displacing the inner sleeve rearwardly as the needle retracts. In this way, the outer sleeve telescopes outwardly extending the length of the housing to accommodate the entire length of the needle.

The housing includes a forward stop to prevent the inner sleeve 1095 from being reinserted into the outer sleeve 1090. The housing further has a rearward stop to prevent the inner sleeve from being displaced rearwardly beyond the rearward edge of the outer sleeve.

A pair of resilient locking tabs 1097 formed in the side of the inner sleeve 1095 cooperate with the rearward edge of the outer sleeve 1090 to operate as the forward stop. The locking tabs 1097 are biased radially outwardly. When the inner sleeve 1095 is enclosed within the outer sleeve 1090, the locking tabs 1097 engage the inner surface of the outer sleeve so that the locking tabs are substantially flush with the outer surface of the inner sleeve. When the inner sleeve is displaced rearwardly so that the locking tabs are rearward of the outer sleeve, the locking tabs flex radially outwardly as shown in FIGS. 38 and 39. Accordingly, attempts to displace the inner sleeve forwardly after retraction causes the locking tabs to engage the rear edge of the outer sleeve, thereby preventing forward displacement.

An annular lip 1093 on the outer sleeve 1090 cooperates with a circumferential flange 1096 on the inner sleeve 1095 to operate as the rearward stop. Referring to FIGS. 38 and 39, the annular lip 1093 projects radially inwardly from the rearward edge of the outer sleeve 1090. The circumferential flange 1096 projects radially outwardly from the forward edge of the inner sleeve 1095. When the inner sleeve is displaced rearwardly, the circumferential flange 1096 engages the annular lip 1093 impeding further rearward displacement of the inner sleeve.

The terms and expressions which have been employed are used as terms of description and not of limitation. There is no intention in the use of such terms and expressions of excluding any equivalents of the features shown and described or portions thereof. It is recognized, however, that various modifications are possible within the scope and spirit of the invention as defined by the claims.

What is claimed is:

1. A medical device, comprising
   a hollow housing;
   a needle having a sharpened tip operable between an extended position extending forwardly from the housing and a retracted position in which the sharpened tip of the needle is enclosed within the housing;
   a catheter mounted on the needle; wherein the catheter comprises a catheter hub;
   a biasing element biasing the needle toward the retracted position; and
   a needle retainer fixedly connected with the insertion needle and releasably retaining the insertion needle in the extended position, comprising a radially deflecting elongated arm which directly engages the catheter hub;

wherein the needle retainer releases the needle upon disengagement of the catheter hub from the elongated arm allowing the elongated arm to deflect inwardly towards the inside of the housing and allowing the biasing element to propel the needle rearward; and wherein when the needle is in the retracted position, the needle retainer is retracted inside the housing.

2. The medical device of claim 1 wherein the elongated arm comprises a latch releasably engaging the housing.

3. The medical device of claim 1 comprising a flashback chamber integrally formed with the needle retainer.

4. A medical device comprising:
a hollow housing;
a needle having a sharpened tip operable between an extended position extending forwardly from the housing and a retracted position in which the sharpened tip is enclosed within the housing;
a catheter mounted on the needle;
a biasing element biasing the needle rearwardly into the retracted position;
a needle retainer operable between a latched position and an unlatched position,
wherein in the latched position the needle retainer retains the needle in the extended position against the bias of the biasing element; and
wherein the needle retainer comprises a radially deflecting elongated arm which directly engages the catheter hub and deflects inwardly toward the inside of the housing to automatically release the needle upon disengagement of the catheter from the housing; and
an exposed surface manually operable to move the needle retainer radially inwardly into contact with a wall of the housing to thereby delay retraction of an inserted needle.

5. The medical device of claim 4 wherein the catheter has an internal surface and an external surface, and a forward portion of the needle retainer engages the catheter external surface.

6. The medical device of claim 4 comprising a fluid chamber in fluid communication with the needle.

7. The medical device of claim 4 wherein the needle retainer is releasably connected to the housing.

8. The medical device of claim 4 wherein a rearward portion of the needle retainer is spaced rearwardly from the catheter.

9. A method for inserting an IV catheter, comprising the steps of:
providing a catheter insertion device having a housing, a catheter hub removably mounted on the housing, a needle, and a needle retainer for releasably retaining the needle so that the needle projects forwardly from the housing, wherein the needle retainer comprises a radially deflecting elongated arm which directly engages the catheter hub;
disengaging the catheter from the housing, wherein the disengagement of the catheter causes the elongated arm of the needle retainer to deflect inwardly toward the inside of the housing thereby causing the needle to begin retracting into the housing;
selectively manually moving the needle retainer radially inwardly into contact with a wall of the housing to thereby impede retraction of the needle;
releasing the selective manual engagement of the needle retainer and the needle; and
deflecting the needle retainer inwardly to retract the needle into the housing.

* * * * *